(12) United States Patent
Perusini

(10) Patent No.: US 11,439,715 B2
(45) Date of Patent: Sep. 13, 2022

(54) COMPOSITIONS AND METHODS TO DETECT GLUA1 IN BRAIN AND TO IDENTIFY THE PRESENCE OF GLUA1-MEDIATED POST-TRAUMATIC STRESS DISORDER AND OTHER NEUROLOGICAL DISORDERS

(71) Applicant: Neurovation Labs, Inc., New York, NY (US)

(72) Inventor: Jennifer Nicole Perusini, New York, NY (US)

(73) Assignee: Neurovation Labs, Inc., New York, NY (US)

( * ) Notice: Subject to any disclaimer, the term of this patent is extended or adjusted under 35 U.S.C. 154(b) by 372 days.

(21) Appl. No.: 16/642,220

(22) PCT Filed: Aug. 28, 2018

(86) PCT No.: PCT/US2018/048250
§ 371 (c)(1),
(2) Date: Feb. 26, 2020

(87) PCT Pub. No.: WO2019/046240
PCT Pub. Date: Mar. 7, 2019

(65) Prior Publication Data
US 2021/0069358 A1    Mar. 11, 2021

Related U.S. Application Data
(60) Provisional application No. 62/550,750, filed on Aug. 28, 2017.

(51) Int. Cl.
| | | |
|---|---|---|
| *A61K 51/00* | (2006.01) | |
| *A61M 36/14* | (2006.01) | |
| *A61K 51/04* | (2006.01) | |
| *A61B 6/00* | (2006.01) | |
| *A61K 9/08* | (2006.01) | |
| *A61K 47/02* | (2006.01) | |
| *C07B 59/00* | (2006.01) | |
| *C07C 211/40* | (2006.01) | |
| *A61B 6/03* | (2006.01) | |

(52) U.S. Cl.
CPC .......... *A61K 51/0497* (2013.01); *A61B 6/501* (2013.01); *A61K 9/08* (2013.01); *A61K 47/02* (2013.01); *C07B 59/001* (2013.01); *C07C 211/40* (2013.01); *A61B 6/037* (2013.01)

(58) Field of Classification Search
CPC ...... A61K 51/0497; A61K 9/08; A61K 47/02; A61K 51/04; A61K 31/137; A61B 6/501; A61B 6/037; C07B 59/001; C07C 211/40
See application file for complete search history.

(56) References Cited

U.S. PATENT DOCUMENTS

| | | |
|---|---|---|
| 2011/0105622 A1 | 5/2011 | Choi et al. |
| 2016/0045625 A1 | 2/2016 | Di et al. |

FOREIGN PATENT DOCUMENTS

| | | |
|---|---|---|
| EP | 2806276 A1 | 11/2014 |
| WO | 2017006931 A1 | 1/2017 |

OTHER PUBLICATIONS

International Search Report and Written Opinion dated Dec. 28, 2018 from International Application No. PCT/US2018/048250.
Bolshakov et al., "Design of Antagonists for NMDA and AMPA Receptors," Neuropharmacology, vol. 49, Issue 2, 2005, pp. 144-155.
Perusini, Thesis and Dissertation titled "The Mechanisms of Fear Sensitization Caused by Acute Traumatic Stress from Induction to Expression to Long-Lasting Reversal," a dissertation submitted in partial satisfaction of the requirements for the degree Doctor of Philosophy in Psychology, University of California, Los Angeles, Jan. 1, 2014, pp. 1-129.
Das et al., "Increased AMPA Receptor GluR1 Subunit Incorporation in Rat Hippocampal CA1 Synapses During Benzodiazepine Withdrawal," The Journal of Comparative Neurology, vol. 511, No. 6, 2008, pp. 832-846.
Zeglis et al., "The Synthesis and Evaluation of N1-(4-(2-[18F]-fluoroethyl)phenyl)-N8-hydroxyoctanediamide ([18F]-FESAHA), a Pe I Radiotracer Designed for the Delineation of Histone Deacetylase Expression in Cancer," Nucl. Med. Biol., vol. 38, No. 5, Jul. 2011, pp. 683-696.
PubChem CID 44561101, Compound Summary for IEM 1925 Dihydrobromide, created on Jan. 26, 2010, 13 pages.

*Primary Examiner* — Michael G. Hartley
*Assistant Examiner* — Melissa J Perreira
(74) *Attorney, Agent, or Firm* — Amster, Rothstein & Ebenstein LLP

(57) ABSTRACT

The present invention provides compositions and methods for detecting GluA1, as a subunit protein and/or as a GluA1-containing, GluA2-lacking AMPAR complex. The invention further provides composition and methods for detecting and/or diagnosing GluA1-mediated disorders, such as PTSD. The invention further relates to compositions that can be detected using radiological imaging techniques, and processes for performing such imaging techniques using the compositions, to identify elevated GluA1 expression or activity in a subject.

20 Claims, 10 Drawing Sheets prior art

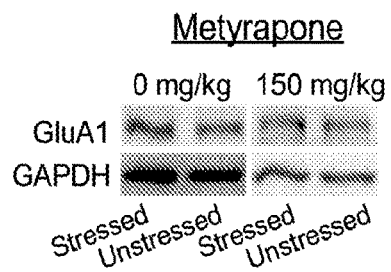
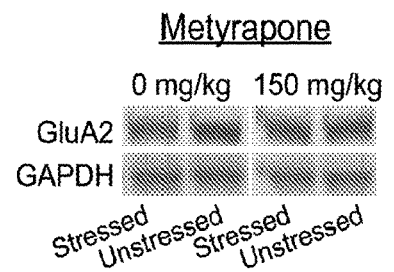
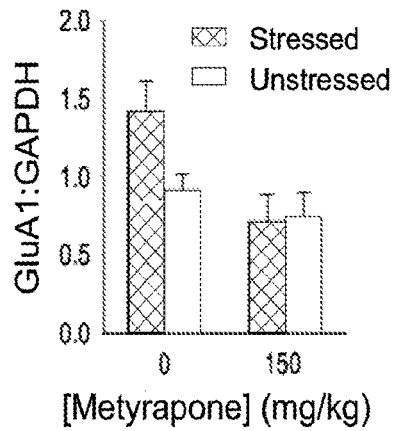
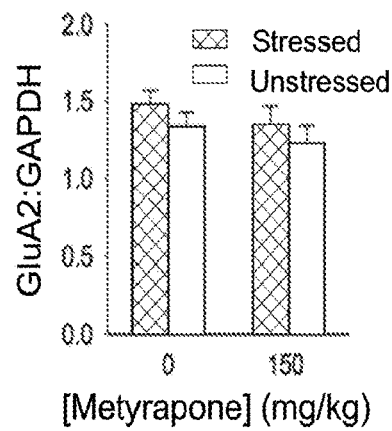
FIG. 2B
FIG. 2C
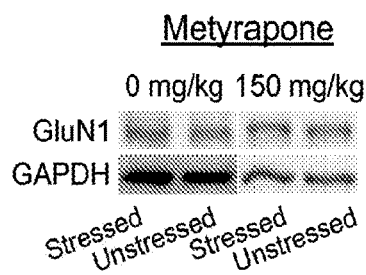
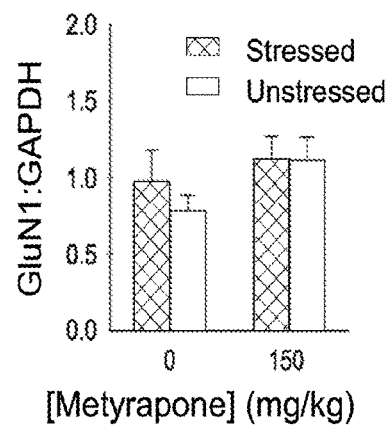
FIG. 2D

COMPOSITIONS AND METHODS TO DETECT GLUA1 IN BRAIN AND TO IDENTIFY THE PRESENCE OF GLUA1-MEDIATED POST-TRAUMATIC STRESS DISORDER AND OTHER NEUROLOGICAL DISORDERS

RELATED APPLICATIONS

This application is a national stage entry of PCT/US18/48250, filed on Aug. 28, 2018, which claims the benefit of U.S. Provisional Application No. 62/550,750, filed on Aug. 28, 2017, and is entitled "COMPOSITIONS AND METHODS TO DETECT GLUA1 IN BRAIN AND TO IDENTIFY THE PRESENCE OF GLUA1-MEDIATED POST-TRAUMATIC STRESS DISORDER AND OTHER NEUROLOGICAL DISORDERS," the contents of each of which are incorporated by reference in their entirety as if fully set forth herein.

BACKGROUND OF THE INVENTION

Glutamate is the major excitatory amino acid neurotransmitter in the mammalian central nervous system that plays a major role in numerous physiological functions, such as learning and memory, synaptic plasticity, sensory perception, motor control, and cardiovascular function. Glutamate signaling is mediated through their activation of either ionotropic glutamate receptor channels (N-methyl-D-aspartate receptors (NMDARs), α-amino-3-hydroxy-5-methyl-4-isoxazolepropionic acid receptors (AMPA receptors or AMPARs), and kainate receptors) responsible for fast excitatory transmission, or metabotropic glutamate receptors (mGluRs) that play a modulatory role in the central nervous system. Glutamate receptors are heteromeric protein complexes formed by multiple subunits that are activated by ligand binding; the classification of each receptor is determined not only by the subunits forming it, but by the type of pharmacological agonist that binds to it.

Glutamate and its corresponding receptors are related to several different neurological and psychiatric diseases. Particularly, GluA1-containing, GluA2-lacking AMPARs, a class of ionotropic glutamate receptor that allows calcium directly through their pores (calcium permeable) and plays a role in synaptic strengthening, are involved in a number of neurological and psychiatric disorders, such as ischemic neurodegeneration, amyotrophic lateral sclerosis (ALS), epilepsy, brain/spinal cord traumatic injury, Alzheimer's, and/or other learning and/or memory disorders implicating calcium permeable AMPARs and/or glutamate (1, 2). Currently, increased functional amygdalar GluA1 protein is being studied as the underlying cause of Post-traumatic Stress Disorder (PTSD). There is typically an abundance of these receptors in the brain, and the present invention enables their in vivo quantification in the brain or one or more regions thereof using nuclear imaging, such as positron emission tomography (PET). PTSD may particularly benefit from this type of tool because it is one of the few aforementioned psychiatric disorders with a region of interest or locus for the GluA1 changes, the amygdala.

PTSD is an incapacitating psychiatric disorder that affects 7-10% of the U.S. population. It develops in 1 in 5 people that experience or witness a traumatic event, such as warfare, natural disasters, and abuse. In a given year, about 7.7 million adults (aged 18-54) will develop PTSD symptoms and at a given time, 24.4 million people have PTSD in the U.S. alone. According to the Department of Veterans Affairs, up to 10% of Gulf War veterans, 20% of Operation Enduring Freedom and Operation Iraqi Freedom veterans, and 30% of Vietnam War veterans have experienced PTSD symptoms. According to recent data, PTSD imposes an annual economic burden exceeding $42 billion, mostly due to misdiagnosis and under-treatment (3).

PTSD symptoms include avoiding stimuli associated with the traumatic event, constant re-experiencing of the event, and increased arousal, exhibited by exaggerated startle response. Under normal circumstances, these symptoms are adaptive for coping with the trauma. For instance, avoiding stimuli associated with the traumatic event lessens the probability of encountering the threat or others like it. However, patients with PTSD lose normal daily functioning because these responses become dysfunctional and exaggerated.

At present, there is no existing biological marker (or biomarker) for PTSD in humans and no objective detection systems or methods. Therefore, the only means for diagnosis of the disease are checklists of symptoms (e.g., using either the Structured Clinical Interview for DSM (SCID)—PTSD Module, or the Clinical Administered PTSD Scale (CAPS)/Life Events Checklist), modeled after symptoms listed in the Diagnostic and Statistical Manual for Mental Disorders (American Psychiatric Association, 2013) (4) (hereby incorporated by reference in its entirety as if fully set forth herein). PTSD is underdiagnosed, partially due to the fact that PTSD is difficult to detect with only checklists and self-report and partially because diagnoses are typically given long after the trauma and after negative effects have manifested in the patient.

Thus, there is a need in the art for compositions and methods for detecting and/or diagnosing PTSD, particularly at a physiological level, as well as other GluA1-mediated psychiatric and neurological disorders, which GluA1-mediated disorders may involve GluA1-containing AMPARs and/or be caused by abnormal levels (e.g., differing from baseline levels) of GluA1-containing AMPARs. Relatedly, there is a need for compositions and methods of detecting in the brain molecular increases of certain proteins known to correspond to presence of PTSD and/or cause PTSD. There is a need for detecting PTSD and other GluA1-mediated disorders or their molecular causes prior to manifestation of symptoms. There is also a need to treat these disorders once a detection and/or diagnosis has been made. Current treatments suppress select symptoms only and/or rely upon therapies to facilitate coping, but comprehensive treatments for PTSD and other disorders that target their physiological causes are lacking. The present invention satisfies these unmet needs.

There is a need to detect GluA1 and GluA1-containing AMPARs in vivo. To date, only post-mortem techniques, such as Western blots, immunohistochemistry, or autoradiography, can detect and/or quantify GluA1 levels or GluA1-containing AMPAR levels. The present invention provides significant advancement over these techniques, enabling in vivo detection and/or quantification of GluA1. While a few mGluR ligands for nuclear imaging have been developed (5), none can detect and distinguish ionotropic glutamate receptors, such as AMPARs, and in particular GluA1-containing AMPARs. There is a need for a detector of GluA1 protein, either individually or in GluA1-containing AMPAR complexes, e.g., to facilitate study and/or detection of GluA1-mediated disorders. To date, most of the available tools targeting glutamate receptors are structural analogues of glutamate that broadly target many different types of glutamate receptors. Therefore, specific ligands must be developed that act on only a single class of glutamate receptor at once to make a highly precise tool of measurement. The present invention further satisfies this unmet need.

SUMMARY OF THE INVENTION

The present invention is generally related to a new tracer, a radiolabeled ligand of GluA2-lacking, calcium permeable AMPARs and/or GluA1-containing AMPARs, designed for use in radiological or nuclear imaging (e.g., diagnostic radiological imaging), which may detect PTSD and/or other GluA1-mediated psychiatric disorders.

The present invention provides a method of detecting a GluA1-mediated disorder, e.g., PTSD, in a subject (e.g., a living subject) comprising administering to the subject a first amount of a radiolabeled composition comprising at least one ligand of a GluA1-containing, GluA2-lacking AMPAR labeled with a radioactive isotope (radioisotope), wherein the radiolabeled composition comprises the following structure:

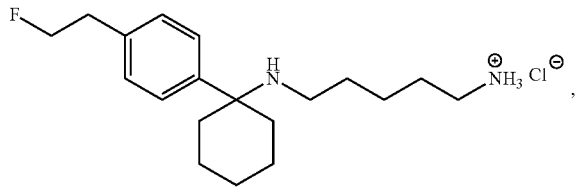

wherein the F is a [$^{18}$F] radioisotope. The method further comprises creating at least one image of a brain (or one or more regions and/or portions thereof) of the subject using positron emission tomography (PET) or single-photon emission computed tomography (SPECT); and determining or quantifying from the at least one image a GluA1-containing, GluA2-lacking AMPAR density in the brain (or in the one or more regions and/or portions thereof) of the subject based at least in part upon an amount of the radiolabeled composition detected in the at least one image, and comparing the density so determined or quantified with a predetermined baseline level, wherein a density different than (e.g., greater than or less than) the predetermined baseline level indicates a disorder in the subject and/or a magnitude of a disorder in the subject. In embodiments, a density different from the pre-determined baseline level by a threshold amount indicates a disorder in the subject. In embodiments, the method may comprise determining and/or quantifying a GluA1-containing, GluA2-lacking AMPAR density in one or more particular regions of the brain of the subject, such as an amygdala. In embodiments, a density in the amygdala greater than the predetermined baseline level may indicate and/or suggest PTSD in the subject. In embodiments, a density in the amygdala less than the predetermined baseline level may indicate a lack of PTSD in the subject.

In embodiments, a baseline or predetermined baseline level (e.g., of GluA1 levels or of GluA1-containing, GluA2-lacking AMPAR levels (e.g., density)) may be determined by performing the imaging detection process on a plurality of subjects known not to be suffering from a GluA1-mediated disorder; determining respective GluA1 levels or GluA1-containing, GluA2-lacking AMPAR levels in the brain or one or more particular regions thereof in each of the plurality of subjects; and computing as the predetermined baseline level a normalized average of the respective GluA1 levels or GluA1-containing, GluA2-lacking AMPAR levels in the brain or in the one or more particular regions thereof in each of the plurality of subjects. In embodiments, the baseline may be an individualized baseline based at least in part upon a level, amount and/or density of GluA1 or GluA1-containing, GluA2-lacking AMPARs in a region of the same brain other than the one or more particular regions of interest, such as a prefrontal cortex, a hippocampus, and/or a cerebellum.

In embodiments described herein, the subject is a living subject. The methods described herein may also be performed on a subject post-mortem. Methods performed post-mortem may comprise administering the radiolabeled composition directly to a region of interest, such as a brain region of interest (e.g., the amygdala), and determining tissue localization of the radiolabeled composition, such as with autoradiography. Such method performed on a non-living subject may further comprise determining GluA1 or GluA1-containing AMPAR density in the brain or in one or more particular brain regions of the subject using autoradiography with the radiolabeled composition.

Also provided is a method of detecting GluA1 levels, or GluA1-containing, GluA2-lacking AMPAR levels in a region of interest (e.g., a brain or particular region(s) thereof, such as an amygdala) of a subject (e.g., a living subject), comprising administering to the subject a first amount of a radiolabeled composition comprising a ligand of GluA1 or a ligand of a GluA1-containing, GluA2-lacking AMPAR effective for detection of the radiolabeled composition in the region of interest of the subject using radiological imaging; and determining or quantifying, by the radiological imaging of the radiolabeled composition in the region of interest of the subject, GluA1 subunit density or GluA1-containing, GluA2-lacking AMPAR density in the region of interest of the subject.

Also provided is a method of detecting a GluA1-mediated disorder, such as PTSD, in a subject, comprising administering to the subject a first amount of a radiolabeled composition comprising a ligand of GluA1 or a ligand of a GluA1-containing, GluA2-lacking AMPAR effective for detection of the radiolabeled composition in a region of interest (e.g., a brain or one or more particular regions thereof, such as an amygdala) of the subject using radiological imaging; and determining or quantifying, by the radiological imaging of the radiolabeled composition in the region of interest of the subject, GluA1 subunit density or GluA1-containing, GluA2-lacking AMPAR density in the region of interest of the subject, and comparing the density so determined or quantified with a predetermined baseline level, wherein a density different than (e.g., greater than or less than) the predetermined baseline level indicates a disorder in the subject. For example, the method may comprise determining or quantifying, by the radiological imaging of the radiolabeled composition in an amygdala of the subject, GluA1 subunit density or GluA1-containing, GluA2-lacking AMPAR density in the amygdala of the subject, and comparing the density so determined or quantified with a predetermined baseline level, wherein a density greater than the predetermined baseline level indicates PTSD in the subject.

Also provided is a method of detecting GluA1-mediated PTSD in a subject, comprising administering to the subject a first amount of a radiolabeled composition comprising a ligand of GluA1 or a ligand of a GluA1-containing, GluA2-lacking AMPAR effective for detection of the radiolabeled composition in an amygdala of a brain of the subject using radiological imaging; and determining or quantifying, by the radiological imaging of the radiolabeled composition in the amygdala of the subject, GluA1 subunit density or GluA1-containing, GluA2-lacking AMPAR density in the amygdala of the subject, and comparing the density so determined or quantified with a predetermined baseline level, wherein a density greater than the predetermined baseline level indicates GluA1-mediated PTSD in the subject.

The present invention also provides a method of detecting GluA1 levels (e.g., GluA1 protein levels), or GluA1-containing, GluA2-lacking AMPAR levels, in a region of interest (e.g., in a brain or one or more regions of interest in a brain) of a subject, comprising administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of the region of interest of the subject using radiological imaging (e.g., PET, SPECT, or another radiological detection and/or imaging system and/or device); and determining or quantifying from the at least one image a GluA1 subunit density or a GluA1-containing, GluA2-lacking AMPAR density in the region of interest of the subject based at least in part upon an amount of the radiolabeled composition detected in the at least one image, so as to detect GluA1 protein levels, or GluA1-containing, GluA2-lacking AMPAR levels, respectively, in the region of interest of the subject.

Also provided is a method of detecting a GluA1-mediated disorder, such as PTSD, in a subject comprising administering to the subject a first amount of a radiolabeled composition comprising at least one ligand of GluA1 labeled with a radioactive isotope or comprising at least one ligand of a GluA1-containing, GluA2-lacking AMPAR labeled with a radioactive isotope; creating at least one image of a region of interest (e.g., a brain or region thereof) of the subject using PET or SPECT or another radiological detection and/or imaging device; and determining or quantifying from the at least one image a GluA1 subunit density or a GluA1-containing, GluA2-lacking AMPAR density in the region of interest of the subject based at least in part upon an amount of the radiolabeled composition detected in the at least one image. In embodiments, the method may further comprise comparing the density so determined or quantified with a predetermined baseline level, wherein a density greater than the predetermined baseline level indicates presence of the disorder in the subject. In embodiments, the method may further comprise providing a diagnosis for the disorder based at least in part upon a determination of whether the GluA1 subunit density or the GluA1-containing, GluA2-lacking AMPAR density in the region of interest either exceeds or is less than the predetermined baseline level by at least a threshold amount. In embodiments PTSD may be detected and/or diagnosed based at least in part upon a determination that the GluA1 subunit density or the GluA1-containing, GluA2-lacking AMPAR density in an amygdala of a brain of the subject exceeds a predetermined baseline level.

In embodiments, the radiolabeled composition may be administered along with a liver-mediated drug metabolism inhibitor, such as disulfiram, miconazole, or another broad-spectrum cytochrome P450 (CYP) inhibitor. Such an inhibitor may prevent or delay metabolism of the radiolabeled composition within the liver by targeting the CYP enzyme class, which can facilitate biodistribution of the radiolabeled composition and a stronger signal in the region of interest, e.g., the amygdala.

The present invention provides a method of treating a GluA1-mediated disorder in a subject comprising receiving information indicating a detection of elevated or reduced levels of GluA1, either alone as a subunit protein or in GluA1-containing, GluA2-lacking calcium permeable AMPAR complexes in a region of interest of the subject, wherein the detection has been obtained by administering to the subject an amount of a radiolabeled composition comprising at least one radiolabeled ligand of GluA1 or comprising at least one radiolabeled ligand of a GluA1-containing, GluA2-lacking AMPAR, the amount of the radiolabeled composition effective to detect the radiolabeled composition in the region of interest of the subject using radiological imaging (e.g., PET or SPECT); determining or quantifying GluA1 levels or GluA1-containing, GluA2-lacking AMPAR levels in the region of interest of the subject; and determining that the GluA1 levels or the GluA1-containing, GluA2-lacking AMPAR levels exceed or are below a predetermined baseline level. The method of treating further comprises administering to the subject an amount of a treatment composition effective to treat the disorder. In embodiments, the treatment composition may be effective to decrease GluA1 expression levels or GluA1-containing, GluA2-lacking AMPAR expression levels in the region of interest. Reducing expression levels may comprise reducing GluA1 levels or GluA1-containing, GluA2-lacking AMPAR levels, or blocking expression of GluA1 or GluA1-containing, GluA2-lacking AMPARs. In embodiments, the treatment composition, depending on the disorder being treated, may be effective to increase GluA1 expression levels or GluA1-containing, GluA2-lacking AMPAR expression levels, e.g., in the region of interest.

In embodiments, the present invention provides a method of treating PTSD in a subject comprising receiving information indicating a detection of elevated levels of GluA1, either alone as a subunit protein or in GluA1-containing, GluA2-lacking calcium permeable AMPAR complexes in an amygdala of the subject, wherein the detection has been obtained by administering to the subject an amount of a radiolabeled composition comprising at least one radiolabeled ligand of GluA1 or comprising at least one radiolabeled ligand of a GluA1-containing, GluA2-lacking AMPAR, the amount of the radiolabeled composition effective to detect the radiolabeled composition in the amygdala of the subject using radiological imaging (e.g., PET or SPECT); determining or quantifying GluA1 levels or GluA1-containing, GluA2-lacking AMPAR levels in the amygdala of the subject; and determining that the GluA1 levels or the GluA1-containing, GluA2-lacking AMPAR levels exceed a predetermined baseline level. The method of treating further comprises administering to the subject an amount of a treatment composition effective to treat PTSD.

In embodiments, the administered treatment composition is effective to reduce GluA1 expression levels or GluA1-containing, GluA2-lacking AMPAR expression levels in the amygdala of a subject. In embodiments, the administered treatment composition is effective to block GluA1-containing, GluA2-lacking AMPARs in the amygdala of a subject. In embodiments, the administered treatment composition is effective to inhibit receptor function of GluA1-containing, GluA2-lacking AMPARs in the amygdala of the subject.

In embodiments described herein, the radiolabeled composition may be molecule 604, 608, 612, 616, 620, 704, 708, 712, 716, or 720 as illustrated in FIGS. 6A-F and 7A-E. The active binding site of the compound is the amine tail, which binds inside the AMPAR pore. The respective radioisotope in each molecule may be stereologically positioned to the cyclic structures opposite the active binding site so as to not interfere with AMPAR binding. Each such compositions may be a radiolabeled detector of a GluA1-containing, GluA2-lacking calcium permeable (α-amino-3-hydroxy-5-methyl-4-isoxazolepropionic acid) receptor. In embodiments, the compositions may each be a radiolabeled detector of GluA1 protein.

Also provided is a compound having the following structure:

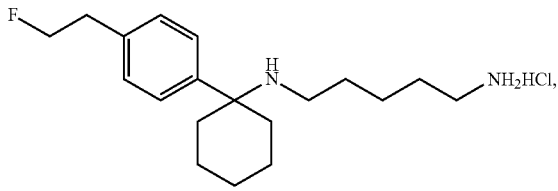

wherein the F is a [18F] radioisotope. The carbon chain connecting the [18F] radioisotope to the phenyl ring comprises two carbons. In embodiments, this chain may comprise a different chain length, such as a chain of one carbon, three carbons, four carbons, and/or five carbons, to name a few. In embodiments, such a carbon chain may comprise one or more double bonds. In embodiments, the [18F] may be attached directly to the phenyl ring without a carbon chain. In embodiments herein, the NH$_2$HCl group is NH$_3$(+)Cl(−), and may be depicted as follows:

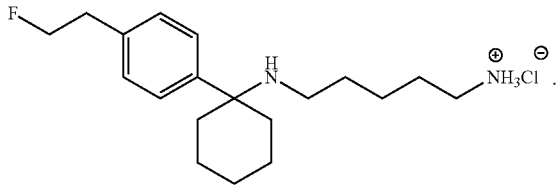

Also provided is a compound having the following structure:

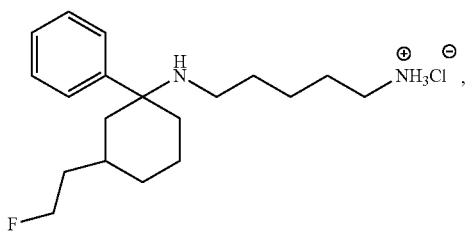

wherein the F is a [18F] radioisotope. The carbon chain connecting the [18F] radioisotope to the cyclohexyl ring comprises two carbons. In embodiments, this chain may comprise a different chain length, such as a chain of one carbon, three carbons, four carbons, and/or five carbons, to name a few. In embodiments, this carbon chain is attached to the cyclohexyl ring at one of at least two possible positions. In embodiments, such a carbon chain may comprise one or more double bonds. In embodiments, the [18F] isotope may be attached directly to the cyclohexyl ring without a carbon chain. In embodiments herein, the NH$_3$Cl group may be a free base such as NH$_2$HCl.

The present invention provides a method of producing a radiolabeled compound comprising performing a radiofluorination reaction on a first compound having the following structure:

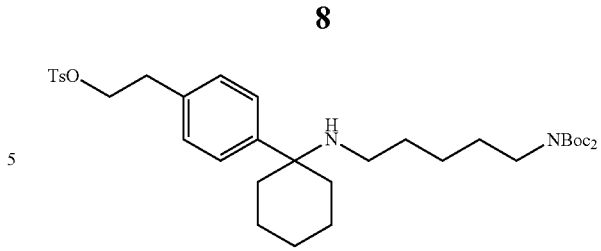

so as to produce a second compound having the following structure:

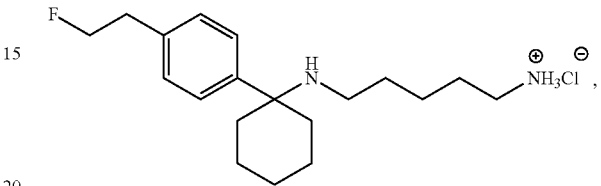

wherein the F is a [18F] radioisotope. In embodiments, the carbon chain connecting the tosylate (TsO) leaving group to the phenyl ring may comprise a different chain length, such as a chain of one carbon, three carbons, four carbons, and/or five carbons, to name a few, and the resulting compound will have the same respective chain length connecting the [18F] radioisotope to the phenyl ring. In embodiments, the chain length may be zero, and the [18F] isotope in the second compound may be attached directly to the phenyl ring. The first compound is a precursor molecule used to synthesize the second compound, which is a radiolabeled composition. The leaving group on the precursor molecule may be iodonium ylide instead of TsO. In embodiments, one or more intermediate molecules between the precursor and final molecule is made.

The present invention provides a method of producing a radiolabeled compound comprising performing a radiofluorination reaction on a first compound having the following structure:

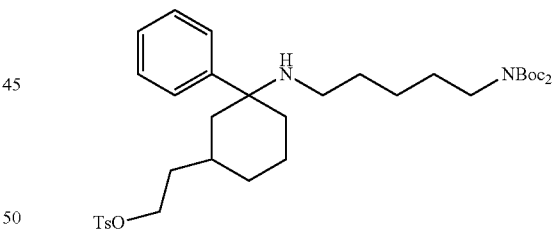

so as to produce a second compound having the following structure:

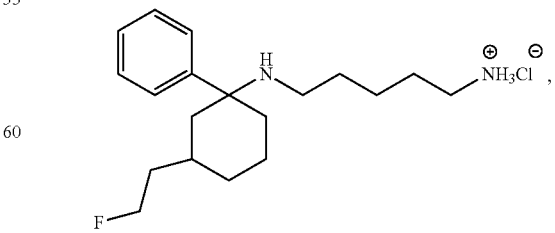

wherein the F is a [18F] radioisotope. In embodiments, the carbon chain connecting the TsO group to the cyclohexyl ring may comprise a different chain length, such as a chain of one carbon, three carbons, four carbons, and/or five carbons, to name a few, and the resulting compound will have the same chain length connecting the [$^{18}$F] radioisotope to the cyclohexyl ring. In embodiments, that carbon chain may be attached to one of at least two possible positions on the cyclohexyl ring. In embodiments, the [$^{18}$F] in the second compound may be attached directly to the cyclohexyl ring without a carbon chain. In embodiments, the leaving group on the first compound may be iodonium ylide instead of TsO. In embodiments, one or more intermediate molecules between the precursor and final molecule may be synthesized.

A method of synthesizing a radiolabeled compound is provided, which comprises obtaining (e.g., producing and/or trapping) an amount of [$^{18}$F]; eluting the [$^{18}$F] with a phase transfer catalyst KF/K2.2.2 so as to produce a solution of [$^{18}$F]KF/K2.2.2 complex; adding a first compound having the following structure:

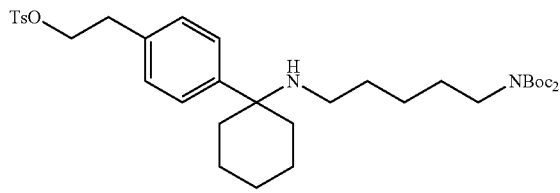

to the solution of [$^{18}$F]KF/K2.2.2 complex so as to perform a radiofluorination reaction to create a second compound having the following structure:

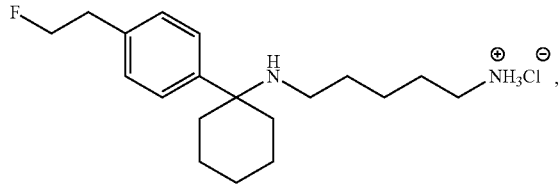

wherein the F is a [$^{18}$F] radioisotope. In embodiments, the method may further comprise purifying the reaction contents from to produce a purified compound radiolabeled with [$^{18}$F]. In embodiments, a subsequent addition of deprotecting agent (e.g., acid) may be added to the reaction vessel and then heated to perform the deprotection reaction to remove Boc groups to form the second compound. In embodiments, purifying the reaction contents can comprise performing radio-HPLC on the product of the radiofluorination reaction. In embodiments, the second compound may be formulated in saline for injection. In embodiments, the first compound and the second compound may have carbon chains of other lengths connecting the TsO and [$^{18}$F] to the phenyl ring respectively. Accordingly, such carbon chains may comprise one carbon, three carbons, four carbons, and/or five carbons, to name a few, or the TsO and [$^{18}$F] can be attached directly to the phenyl ring without a respective carbon chain. In embodiments, the first compound may comprise an iodonium ylide leaving group instead of TsO.

A method of synthesizing a radiolabeled compound is provided, which comprises obtaining (e.g., producing and/or trapping) an amount of [$^{18}$F]; eluting the [$^{18}$F] with a phase transfer catalyst KF/K2.2.2 so as to produce a solution of [$^{18}$F]KF/K2.2.2 complex; adding a first compound having the following structure:

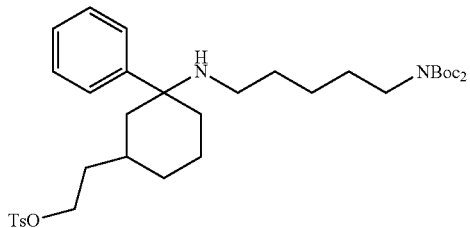

to the solution of [$^{18}$F]KF/K2.2.2 complex so as to perform a radiofluorination reaction to create a second compound having the following structure:

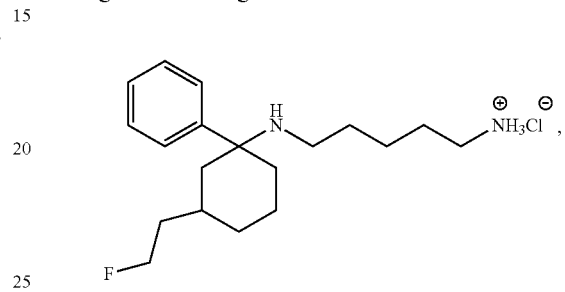

wherein the F is a [$^{18}$F] radioisotope. In embodiments, the method may further comprise purifying the reaction contents from to produce a purified compound radiolabeled with [$^{18}$F]. In embodiments, a subsequent addition of deprotecting agent (e.g., acid) is added to the reaction vessel and then heated to perform the deprotection reaction to remove Boc groups to form the final molecule. In embodiments, purifying the reaction contents can comprise performing radio-HPLC on the product of the radiofluorination reaction. In embodiments, the final molecule may be formulated in saline for injection. In embodiments, the first compound and the second compound may have carbon chains of other lengths connecting the TsO and F to the cyclohexyl ring respectively. Accordingly, such carbon chains may comprise one carbon, three carbons, four carbons, and/or five carbons, to name a few, or the TsO and [$^{18}$F] can be attached directly to the cyclohexyl ring without a respective carbon chain. In embodiments, the precursor may comprise an iodonium ylide leaving group instead of TsO.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 2B-D depict representative Western blot images and graphs of relative optical density ratios(±standard error of the mean (SEM)) of GluA1, GluA2, and GluN1, respectively, and a glyceraldehyde 3-phosphate dehydrogenase (GAPDH) control. These figures show the results of example experiments demonstrating that there are observed long-term increases in GluA1 protein in the basolateral amygdala (BLA) after a traumatic event. Glutamate receptor protein changes were measured three weeks after the initial trauma via Western blotting. While the GluA2 subunit of the AMPAR and the GluN1 subunit of the NMDAR remained unchanged after trauma, GluA1 increased substantially. Metyrapone, a cortisol/corticosterone-synthesis blocker given before the trauma effectively preventing SEFL also prevented GluA1 increases and conferred levels to that of unstressed controls.

DETAILED DESCRIPTION

Figure 1A:
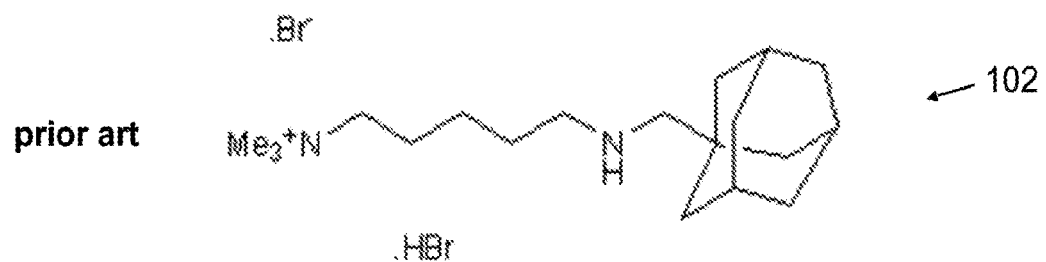
FIGS. 1A-B depict prior art AMPAR ligands highly selective for blocking GluA1-containing, GluA2-lacking AMPARs.

The present invention relates generally to compositions and methods for detecting levels (e.g., densities) of GluA1 (also referred to as GluR1), either alone as a subunit protein or within GluA1-containing, GluA2-lacking AMPAR complexes in a region of interest (e.g., a brain or one or more regions thereof) of a subject (e.g., a human subject). The compositions and methods may comprise use of imaging techniques (e.g., diagnostic and/or radiological imaging techniques) involving imaging agents designed to target GluA1 and/or GluA1-containing and/or GluA2-lacking AMPARs in the brain. In embodiments, the compositions and methods of the present invention can enable detection and/or diagnosis of learning or memory disorders implicating calcium permeable AMPARs and/or glutamate, such as PTSD, ischemic neurodegeneration, amyotrophic lateral sclerosis (ALS), epilepsy, brain/spinal cord traumatic injury, and/or Alzheimer's, to name a few. For example, with PTSD the region of interest is the amygdala of the brain, where increased levels of GluA1 or of GluA1-containing, GluA2-lacking AMPARs can indicate the presence of PTSD in a subject. In embodiments, such detection and/or diagnosis is physiology-based and/or objective.

AMPARs are composed of four types of protein subunits, which are designated as GluA1, GluA2 (also referred to as GluR2), GluA3 (also referred to as GluR3), and GluA4 (also referred to as GluR4) (6). The HUGO gene nomenclature committee refers to the encoding gene for GluA1 as HGNC: 4571, and for GluA2 as HGNC:4572. GluA1 is at times referred to by the gene name, GRIA1, which produces GluA1 protein when translation is activated (e.g., by a learning event). The GRIA2 gene produces GluA2 protein when translation is activated. Non-limiting exemplary GRIA1 sequences include NCBI Reference Sequences: NM000827.3, NM001258023.1 and NM001258022.1. Non-limiting exemplary GRIA2 sequences include NCBI Reference Sequences: NM000826.3, NM001083620.1, and NM001083619.1.

The AMPAR subunits combine to form tetramers, protein polymers composed of four monomer units. The presence of a GluA2 subunit will almost always render the receptor channel impermeable to calcium, meaning that the neurons on which these AMPARs are located are more difficult to depolarize, transduce signals, and/or communicate with neighboring neurons. Without cell activity, GluA2/GluA3-containing AMPARs are more commonly located at the synapse because of their stability to be tethered to the cell membrane. On the other hand, GluA1-containing AMPARs are important for cell plasticity and are brought to cell synapses in the presence of cell activity to strengthen cell connections. GluA1-containing AMPARs that are lacking GluA2 are commonly found in areas important for learning and memory and particularly fear learning and memory, such as the hippocampus and the amygdala. Enrichment of synaptic GluA2-lacking AMPARs (typically found as GluA1 homomers and GluA1/GluA3 heteromers), as well as synaptic insertion of GluA1 in these regions underlies long-term potentiation (LTP), a process by which recent patterns of activity cause persistent strengthening of synapses, which is crucial for long-term memory formation. Blocking the formation of GluA1 protein will effectively block the formation of functional GluA1-containing AMPARs after a learning event and/or potentially block LTP/long-term memory formation (7).

The present inventions provides radiolabeled compositions that can serve as radiolabeled detectors of GluA1, either alone as a subunit protein or as part of a GluA1-containing, GluA2-lacking calcium permeable AMPAR complex, which may be a human AMPAR. Accordingly compositions provided by the present invention may each comprise at least one radiolabeled detector of a GluA1-containing, GluA2-lacking calcium permeable AMPAR. In embodiments, the compositions may comprise at least one radiolabeled detector of GluA1 protein, e.g., as a subunit protein. In embodiments, the radiolabeled detectors may be detectors of GluA1 expression, surface expression, AMPAR activity, or a combination thereof. In embodiments, the radiolabeled detectors may be inhibitors of AMPAR activity or of AMPAR function (e.g., inhibiting ionic influx through the AMPAR, inhibiting agonist binding of the AMPAR, inhibiting pore opening of the AMPAR, enhancing pore blocking of the AMPAR, inhibiting calcium influx of the AMPAR, or a combination thereof). In embodiments, such inhibitors may be inhibitors of calcium-permeable AMPAR function. Methods of the present invention comprise detecting levels of GluA1-containing and/or GluA2-lacking AMPARs by proxy of radioactive emissions from a radiolabeled composition.

The radiolabeled detectors may comprise a ligand of GluA1 or of a GluA1-containing, GluA2-lacking calcium permeable AMPAR. In embodiments, the radiolabeled detectors may be selected from the group consisting of a nucleic acid, an antisense oligonucleotide (e.g., GluA1 ASO), a ribozyme, a peptide, a small molecule (e.g., a molecule of an organic compound having a low molecular weight (e.g., less than 900 daltons) that may help regulate a biological process, with a size on the order of 1 nm), an antagonist, an aptamer, and a peptidomimetic, radiolabeled with a radioisotope and/or a positron-emitting radionuclide. The radiolabeled detectors may comprise a radioisotope, such as [$^{18}$F], [$^{11}$C], [$^{13}$N], [$^{15}$O], [$^{123}$I$^{-}$], [$^{124}$I], [$^{131}$I], [$^{38}$K], [$^{62}$Cu], [$^{64}$Cu], [$^{68}$Ga], [$^{82}$Rb], [$^{99m}$Tc], [$^{133}$Xe], or [$^{201}$Tl]. The radioisotope may be a positron-emitting radionuclide. Accordingly, the radiolabeled detectors may comprise a positron-emitting radionuclide. In embodiments for PET, the compounds of the present invention may be radiolabeled with positron-emitting isotopes, including but not limited to [$^{18}$F]fluorine, [$^{124}$I]iodine, [$^{11}$C]carbon, [$^{15}$O]oxygen, [$^{13}$N]nitrogen, or [$^{76}$Br]bromide, using organic chemistry and/or radiochemistry methods. For SPECT, the compounds may be labeled with [$^{99m}$Tc]technetium, [$^{123}$I]iodine, or [$^{131}$I]iodine, using organic chemistry and/or radiochemistry methods. In embodiments, these radioisotopes may replace the [$^{18}$F] radioisotope in the compositions of the present invention.

In embodiments, the present invention provides a radiolabeled composition comprising a radiolabeled ligand of GluA1 or a radiolabeled ligand of a GluA1-containing, GluA2-lacking AMPAR for use in a method of in vivo detection and/or quantification of GluA1 levels, or GluA1-containing, GluA2-lacking AMPAR levels in one or more regions of interest of a subject. In embodiments, the present invention provides a radiolabeled composition comprising a radiolabeled ligand of GluA1 or a radiolabeled ligand of a GluA1-containing, GluA2-lacking AMPAR for use in a method of in vivo detection and/or diagnosis of a GluA1-mediated disorder, such as PTSD, in a subject, as described herein. In embodiments, the radiolabeled composition may be brain penetrant, e.g., having the ability to cross the blood brain barrier. The composition may be effective to cross a blood-brain barrier of the subject to enter a region of interest in the brain following administration to the subject.

The radiolabeled composition may comprise an inhibitor of GluA1, which is a compound, molecule, or agent that reduces, inhibits, or prevents the expression or function of GluA1. For example, an inhibitor of GluA1 may be a compound, molecule, or agent that reduces GluA1 expression, surface expression, activity, or a combination thereof. In certain embodiments, such an inhibitor can inhibit the transcription of DNA, inhibit the translation of RNA, and/or inhibit the protein itself. In embodiments, an inhibitor of GluA1 comprises a peptide, an antibody, a small molecule, a ribozyme, an antagonist, an aptamer, an allosteric modulator, a peptidomimetic, or any combination thereof.

The radiolabeled composition may comprise an agonist or activator of GluA1, which is a compound, molecule, or agent that increases or stimulates the expression or function of GluA. For example, an agonist of GluA1 is a compound, molecule, or agent that increases GluA1 expression, surface expression, activity, or a combination thereof. In certain embodiments, the agonist increases the transcription of DNA, increases the translation of RNA, or activates the protein itself. In embodiments, an agonist of GluA1 comprises a peptide, an antibody, a small molecule, a ribozyme, an aptamer, a peptidomimetic, or any combination thereof.

In embodiments, the radiolabeled composition may comprise an allosteric modulator of GluA1-containing and/or GluA2-lacking calcium permeable AMPARs. For example, in one embodiment, the composition activates GluA1-containing AMPAR activity by binding to a binding site distinct from the true ligand, which is glutamate. In embodiments, the composition may comprise a positive allosteric modulator to amplify the signal of the true ligand (glutamate). In embodiments, the composition may comprise a negative allosteric modulator to reduce the effect of the true ligand.

In embodiments, the radiolabeled composition may comprise a competitive or non-competitive (or allosteric) agonist of GluA1-containing and/or GluA2-lacking calcium permeable AMPARs. In embodiments, the composition activates the activity of GluA2-lacking, calcium permeable AMPARs by binding to the primary binding site. In certain embodiments, the agonist may increase ionic influx through the AMPAR, inhibit antagonist and true ligand binding of the AMPAR, increase pore opening of the AMPAR, reduce pore blocking of the AMPAR, increase calcium influx of the AMPAR, or a combination thereof. In other embodiments, the composition directly activates GluA1-containing, GluA2-lacking AMPARs by binding to an allosteric agonist binding site distinct from the primary site and exerts its effect in the absence of the true ligand (glutamate).

In embodiments, the radiolabeled composition may comprise a competitive or non-competitive (or allosteric) antagonist of GluA1-containing and/or GluA2-lacking calcium permeable AMPARs. In embodiments, the composition may inhibit the activity of GluA2-lacking, calcium permeable AMPARs by binding to the primary binding site. In certain embodiments, the antagonist may decreases ionic influx through the AMPAR, inhibit agonist and true ligand binding of the AMPAR, decrease pore opening of the AMPAR increase pore blocking of the AMPAR decrease calcium influx of the AMPAR or a combination thereof. In other embodiments, the composition may directly inhibit GluA1-containing, GluA2-lacking AMPARs by binding to an allosteric antagonist binding site distinct from the primary site and exerts its effect in the absence of the true ligand (glutamate).

FIGS. 6A-F and 7A-E depict molecular structures for exemplary compositions provided by the present invention. The compositions may be radiolabeled compositions, radiolabeled detectors, tracers (e.g., radioactive tracers), and/or imaging agents, which may comprise the structures 604, 608, 612, 616, 620, 704, 708, 712, 716, or 720, wherein the F is a [$^{18}$F] isotope. In embodiments, the respective radiolabeled compositions or radiolabeled detectors required in the methods described herein may thus comprise the molecular structures of these compounds 604, 608, 612, 616, 620, 704, 708, 712, 716, or 720. In embodiments, stereoisomers, tautomers, and/or pharmaceutically acceptable salts of compounds 604, 608, 612, 616, 620, 704, 708, 712, 716, or 720 are provided and may serve as radiolabeled compositions for the methods described herein. In embodiments, the radiolabeled compositions used in the methods of the present invention may comprise combinations of stereoisomers, tautomers, and/or pharmaceutically acceptable salts of compounds 604, 608, 612, 616, 620, 704, 708, 712, 716, or 720.

Figure 6A:
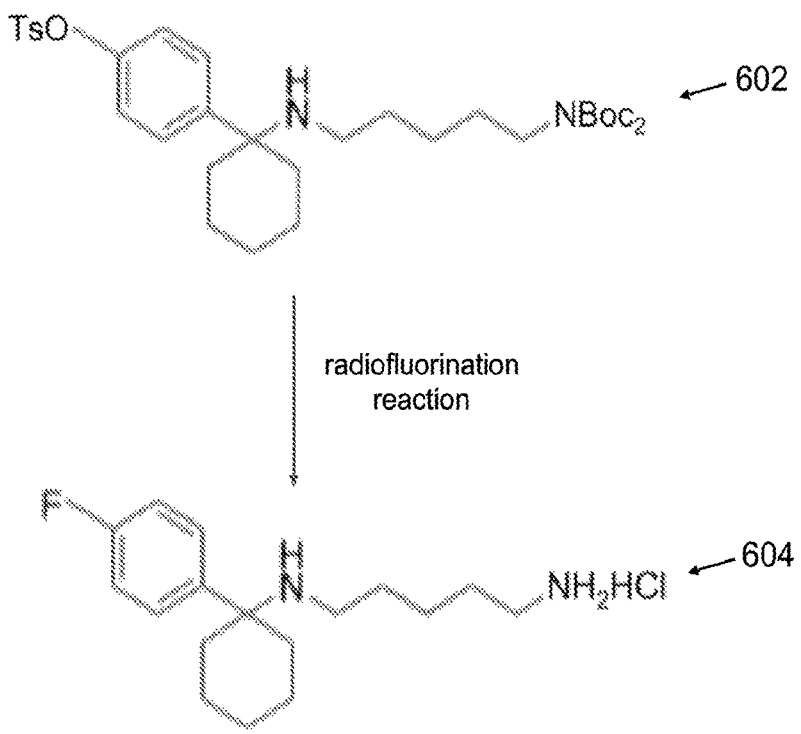
FIGS. 6A-F are flowcharts illustrating exemplary processes for synthesizing radiolabeled compositions in exemplary embodiments of the present invention.
Figure 6B:
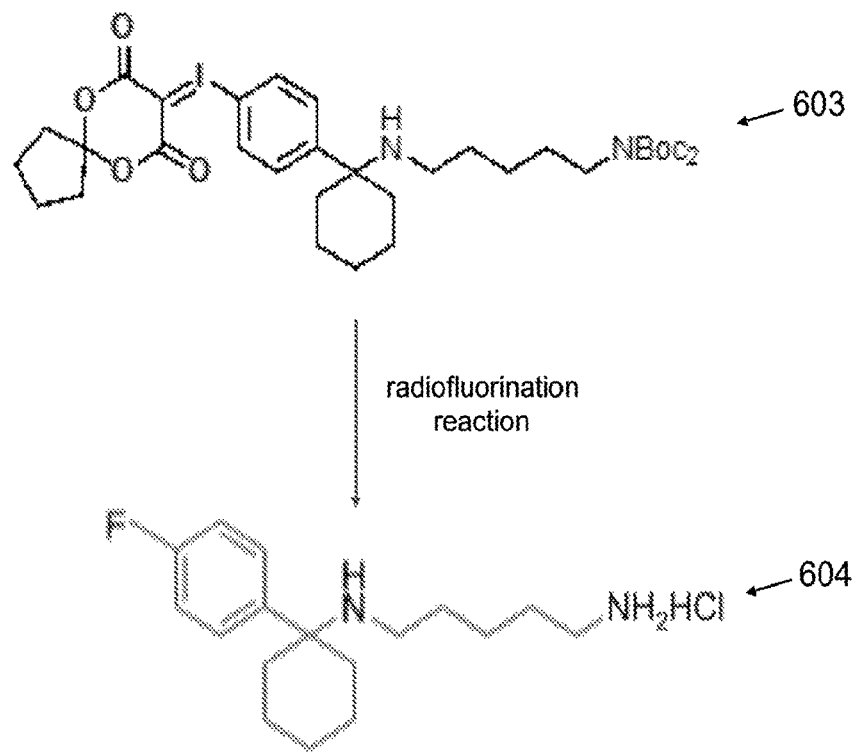
Figure 6C:
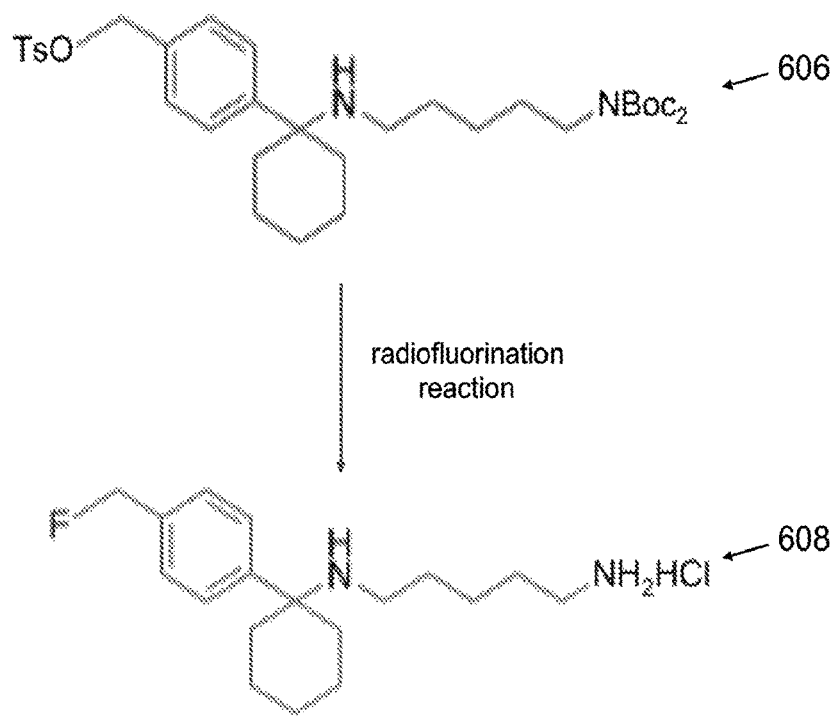
Figure 6D:
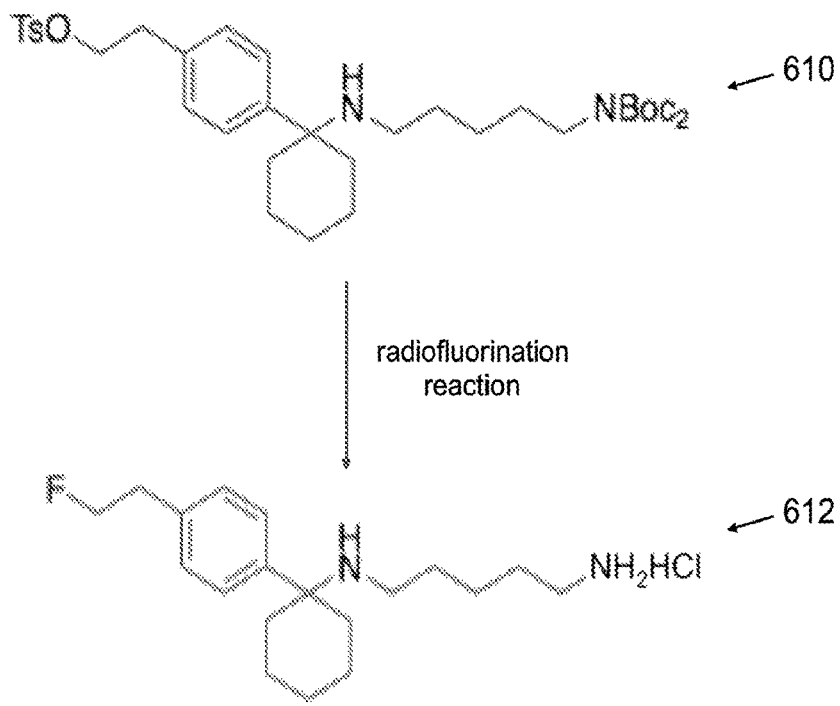
Figure 6E:
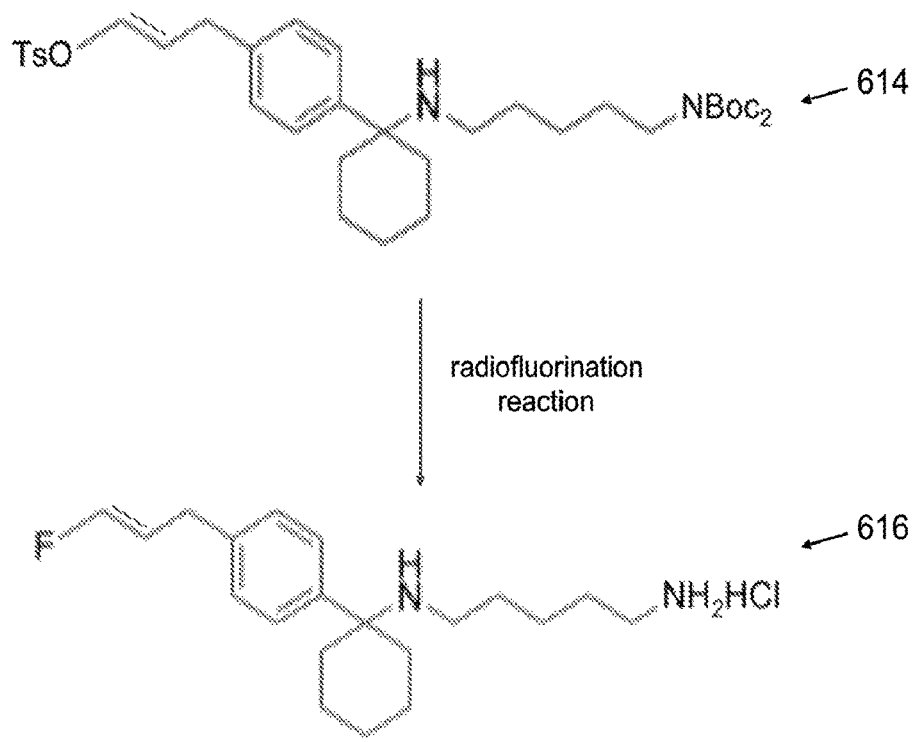
Figure 6F:
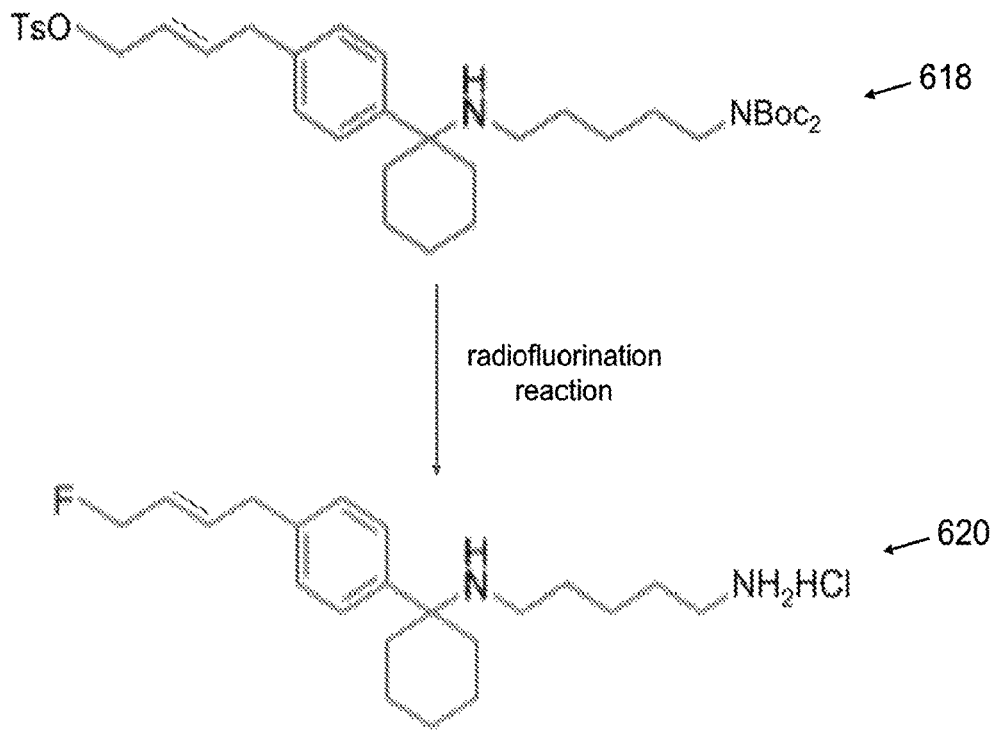

FIGS. 6A-F show variants of a structure with the radioisotope attached to a phenyl ring by different chains. In FIGS. 6A and 6B, structure 604 comprises a [$^{18}$F] isotope attached directly to the phenyl ring without a carbon chain. In embodiments, attaching the [$^{18}$F] isotope directly to the cyclohexyl ring may increase stability and/or increase time to defluorination. In FIG. 6C, structure 608 has a one carbon chain attaching a [$^{18}$F] isotope to the phenyl ring. In FIG. 6D, structure 612 has a two carbon chain attaching a [$^{18}$F] isotope to the phenyl ring. In embodiments, this radiolabeled detector comprises 5-((1-(4-(2-fluoroethyl)phenyl)cyclohexyl)amino)pentan-1-aminium. In FIG. 6E, structure 616 has a three carbon chain attaching a [$^{18}$F] isotope to the phenyl ring. In FIG. 6F, structure 620 has a four carbon chain attaching a [$^{18}$F] isotope to the phenyl ring. In embodiments, as seen in structures 616 and 620, the carbon chain attaching [$^{18}$F] may comprise one or more double bonds, which may exist at locations in the chain other than those shown. In embodiments, the carbon chain may have no double bonds (e.g., the chain may comprise only single bonds). In embodiments, other chain lengths are possible, such as a five carbon chain. In embodiments, the NH$_2$HCl group is NH$_3$(+)Cl(−), e.g., the compound is a salt.

Figure 7A:
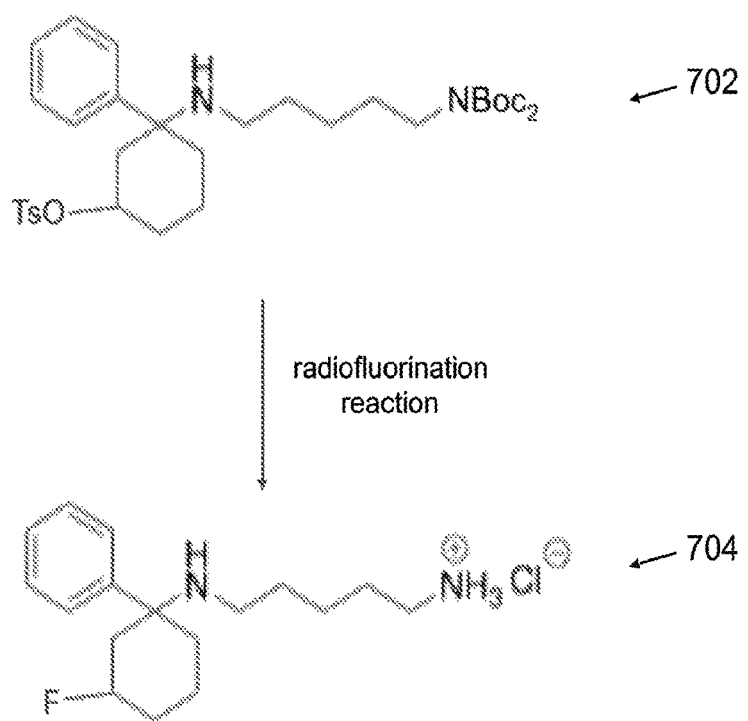
FIGS. 7A-E are flowcharts illustrating exemplary processes for synthesizing radiolabeled compositions in exemplary embodiments of the present invention.
Figure 7B:
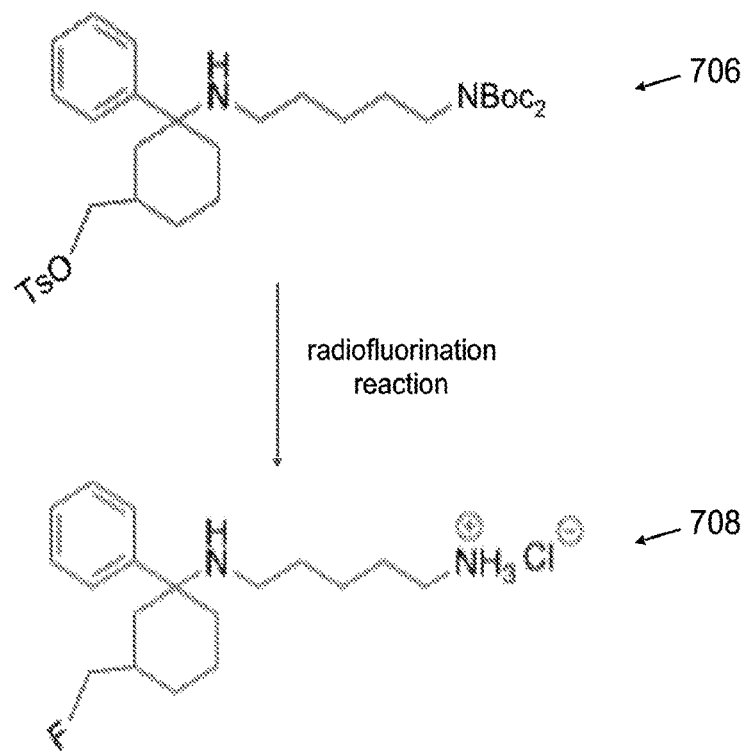
Figure 7C:
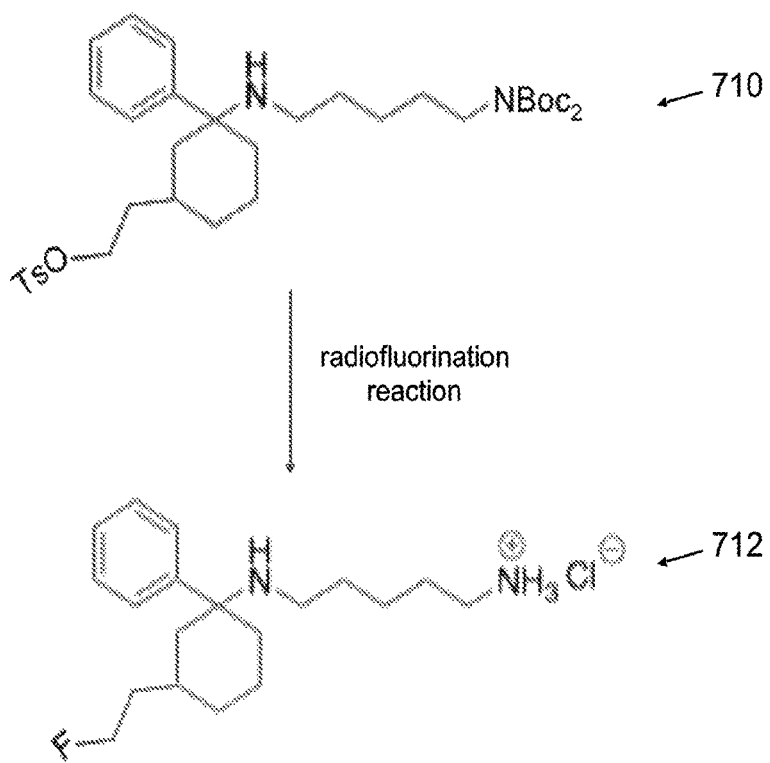
Figure 7D:
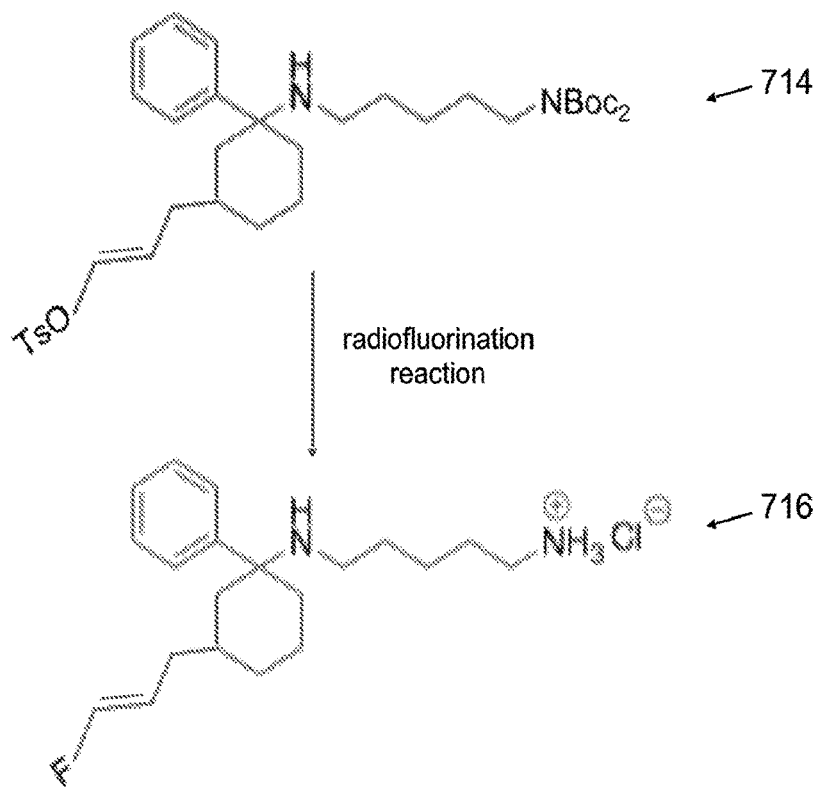
Figure 7E:
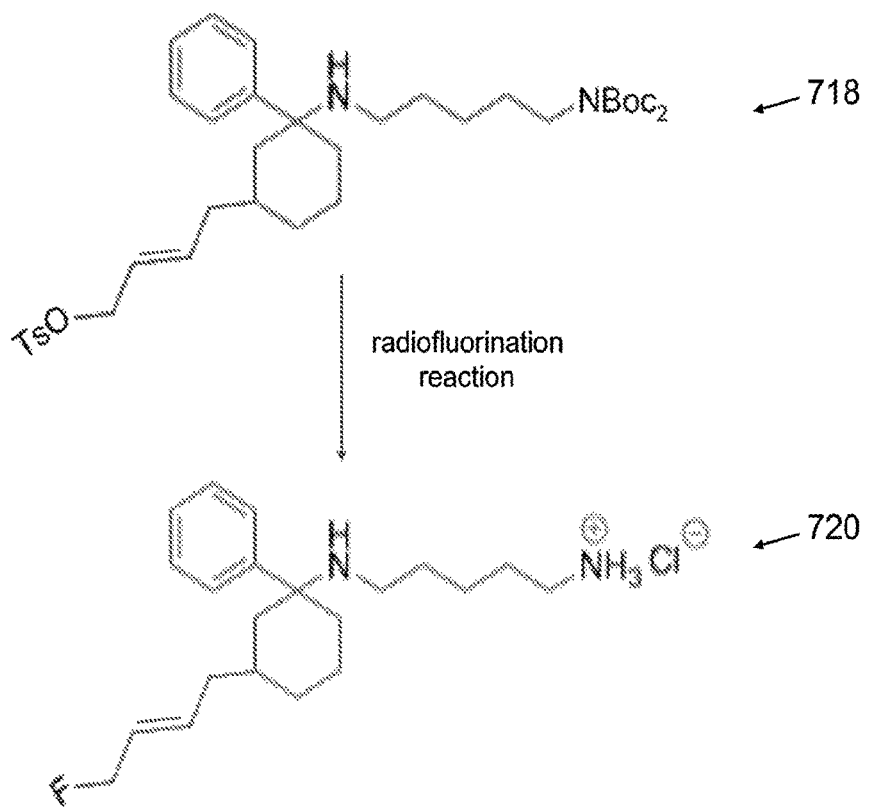

FIGS. 7A-E show variants of a structure with the radioisotope attached to a cyclohexyl ring by different chains. In FIG. 7A, structure 704 comprises a [$^{18}$F] isotope attached directly to the cyclohexyl ring without a carbon chain. In embodiments, attaching the [$^{18}$F] isotope directly to the cyclohexyl ring may increase stability and/or increase time to defluorination. In FIG. 7B, structure 708 has a one carbon chain attaching [$^{18}$F] isotope to the cyclohexyl ring. In FIG. 7C, structure 712 has a two carbon chain attaching a [$^{18}$F] isotope to the cyclohexyl ring. In FIG. 7D, structure 716 has a three carbon chain attaching a [$^{18}$F] isotope to the cyclohexyl ring. In FIG. 7E, structure 720 has a four carbon chain attaching a [$^{18}$F] isotope to the cyclohexyl ring. In embodiments, as seen in structures 716 and 720, the carbon chain attaching [$^{18}$F] may comprise one or more double bonds, which may exist at locations in the chain other than those shown. In embodiments, the carbon chain may have no double bonds. In embodiments, other chain lengths are possible, such as a five carbon chain. In embodiments, the carbon chain attaching the [$^{18}$F] isotope to the cyclohexyl ring may be attached to the cyclohexyl ring at one of at least two possible positions. In embodiments, the NH$_3$(+)Cl(−) group is NH$_2$HCl, e.g., the compound is a free base.

In embodiments, a longer carbon chain, such as a three or four carbon chain, linking the [$^{18}$F] isotope to the phenyl ring or cyclohexyl ring respectively may provide greater stability and/or decrease defluorination, e.g., preventing or decreasing in vivo defluorination following administration, compared to shorter carbon linking chains. In the longer chains, the position of the [$^{18}$F] farther away from the phenyl ring or cyclohexyl ring respectively can prevent or reduce electron sharing interactions on the base of the molecule. Additionally, the longer carbon chains comprise more bonds than the structures with shorter chains, and the higher number of bonds can result in greater strength holding the [$^{18}$F] to the molecule.

In embodiments, the composition may comprise a solution of the radiolabeled detector, such as a saline solution and/or an ethanol solution. In embodiments, a solution comprising the radiolabeled detector may be diluted, e.g., with water or saline. The composition may be put into a solution, e.g., for storage and/or administration. For example, a saline solution comprising the radiolabeled detector may be administered to a subject. Such a solution may be at or near room temperature. Accordingly, in embodiments, the compounds 604, 608, 612, 616, 620, 704, 708, 712, 716, or 720 each may compose a respective solution, such as a saline solution or an ethanol solution.

In embodiments, the compounds 604, 608, 612, 616, 620, 704, 708, 712, 716, or 720 may each be suitable as a radiolabeled tracer in one or more imaging detection processes. In embodiments, the radiological imaging and/or imaging detection processes may be used to determine whether the GluA1 protein or the GluA1-containing, GluA2-lacking AMPARs exceed a predetermined baseline level and/or to determine an amount by which the GluA1 protein or the GluA1-containing, GluA2-lacking AMPARs exceed the predetermined baseline level. In embodiments, the radiological imaging and/or imaging detection processes may be usable to detect PTSD in a subject.

In embodiments, the composition can serve as a radiolabeled tracer in an imaging detection process for living subjects, e.g., radiological or nuclear imaging, such as PET, SPECT, or other radiological sensing and/or imaging. Any such radiological imaging may comprise detection of radioactive emissions (e.g., gamma rays), which, in embodiments, may be performed by a portable device (e.g., a portable sensing device) and/or in a clinical setting. Accordingly, in embodiments described herein the subject may be a living subject (e.g., the method of the present invention may be performed in vivo). In embodiments, the composition can serve as a radiolabeled probe in autoradiography in post-mortem tissue. In embodiments, the imaging detection process may be used to quantify and/or determine expression (e.g., levels, amounts, and/or densities) of GluA1 protein or of GluA1-containing, GluA2-lacking AMPARs in a region of a subject. In embodiments, the region of the subject is a brain of the subject and/or one or more portions of the brain, such as an amygdala. In embodiments, amygdala refers to both a left amygdala and a right amygdala together. In embodiments, only a portion of the amygdala is studied, imaged, and/or examined, such as the left portion or the right portion, which may include one or more nuclei on either side of the amygdala. In embodiments, the amygdala as described herein is the BLA, which may be a left BLA, a right BLA, or both a left and a right BLA. In embodiments, the subject is a human subject. In embodiments, the subject is another mammal, including, but not limited to, a primate, cow, horse, sheep, goat, dog, cat, rodent, and the like. In embodiments, the imaging detection process may be used to determine whether the GluA1 protein itself or the GluA1-containing, GluA2-lacking AMPARs exceed a predetermined baseline level. In embodiments, the imaging detection process may be used to determine a degree to which and/or an amount by which the GluA1 protein or the GluA1-containing, GluA2-lacking AMPARs exceed a predetermined baseline level.

In embodiments, the imaging detection process may be used to determine whether the GluA1 protein itself or the GluA1-containing, GluA2-lacking AMPARs are lower than a predetermined baseline level. In embodiments, the imaging detection process may be used to determine a degree to which and/or an amount by which the GluA1 protein or the GluA1-containing, GluA2-lacking AMPARs are lower than a predetermined baseline level.

In embodiments, the imaging detection process may be usable to detect and/or diagnose a GluA1-mediated psychological disorder in a subject, e.g., based on detected levels (e.g., densities) of GluA1, either alone as a subunit protein or in GluA1-containing, GluA2-lacking calcium permeable AMPAR complexes in a region of interest of a subject, and/or further based upon a comparison to one or more baseline levels (e.g., baseline densities) or threshold levels.

One such disorder is PTSD, where the region of interest is the amygdala. In embodiments, a region of interest in the methods provided herein may comprise one or more regions of interest, such as one or more regions of the brain or portions of the brain, e.g., a left amygdala, a right amygdala, a left hippocampus, a right hippocampus, a prefrontal cortex, a cerebellum, and/or portions thereof, to name a few. The radiolabeled compositions provided herein can enable multiple hour, entire-body radiological imaging of a subject, and/or imaging of a targeted region. While the region of interest for PTSD may be the amygdala, imaging of other body regions is possible, including other brain regions. Imaging of other regions may be desirable to study, detect, and/or diagnose other disorders implicating calcium permeable AMPARs and/or glutamate.

The present invention further provides a method of detecting a GluA1-mediated disorder (e.g., PTSD) in a subject, comprising administering to the subject a first amount of a radiolabeled composition comprising at least one ligand of a GluA1-containing, GluA2-lacking AMPAR labeled with a radioisotope, wherein the radiolabeled composition comprises the following structure:

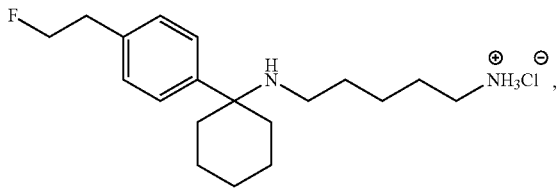

wherein the F is a [$^{18}$F] radioisotope. In embodiments, the radiolabeled composition may instead comprise one of structures 604, 608, 612, 616, 620, 704, 708, 712, 716, or 720. The method may further comprise creating at least one image of a brain of the subject using radiological imaging (e.g., PET or SPECT); and determining or quantifying from the at least one image a GluA1-containing, GluA2-lacking AMPAR density in a region of interest (e.g., the brain or one or more particular regions thereof, such as the amygdala) of the subject based at least in part upon an amount of the radiolabeled composition detected in the at least one image, and comparing the density so determined or quantified with a predetermined baseline level, wherein a density different than (e.g., greater than or less than) the predetermined baseline level indicates the GluA1-mediated disorder in the subject.

A method of detecting GluA1, either alone as a subunit protein or in GluA1-containing, GluA2-lacking calcium permeable AMPAR complexes in a region of interest of a subject, such as a brain or one or more regions thereof (e.g., an amygdala, a hippocampus, a prefrontal cortex, and/or a cerebellum), is provided. In embodiments, the method of detecting GluA1 (e.g., GluA1 levels and/or GluA1 subunit density) or GluA1-containing, GluA2-lacking AMPARs (e.g., GluA1-containing, GluA2-lacking AMPAR levels and/or density) may comprise administering to the subject a first amount of a radiolabeled composition (e.g., a tracer or radiotracer) comprising a ligand of GluA1 or a ligand of a GluA1-containing, GluA2-lacking AMPAR effective for detection of the radiolabeled composition in the region of interest of the subject using radiological imaging (e.g., PET or SPECT); and determining or quantifying, by the radiological imaging of the radiolabeled composition in the region of interest of the subject, GluA1 subunit density or GluA1-containing, GluA2-lacking AMPAR density in the region of interest of the subject.

In embodiments, a method of detecting GluA1 levels, or GluA1-containing, GluA2-lacking AMPAR levels, in a region of interest of a subject may comprise determining or quantifying GluA1 subunit density or GluA1-containing, GluA2-lacking AMPAR density in the region of interest by radiological imaging the region of interest (e.g., to determine or quantify radioactive emission levels or densities in the region of interest), wherein a first amount of a radiolabeled composition effective for detection of the radiolabeled composition (e.g., via its radioactive emissions) in the region of interest of the subject using radiological imaging has been administered to the subject.

In embodiments, a method of detecting a GluA1-mediated psychological disorder may comprise administering to a subject a first amount of a radiolabeled composition effective for detection of the radiolabeled composition in a region of interest (e.g., a brain or one or more region thereof, such as an amygdala) of the subject using radiological imaging; and determining or quantifying, by the radiological imaging of the radiolabeled composition in the region of interest of the subject, GluA1 subunit density or GluA1-containing, GluA2-lacking AMPAR density in the region of interest of the subject, and comparing the density so determined or quantified with a predetermined baseline level, wherein a density different from the predetermined baseline level and/or different from the predetermined baseline level by at least a threshold amount indicates the GluA1-mediated disorder in the subject. In embodiments, a density within a predetermined amount (e.g., absolute amount or percentage) from the predetermined baseline level indicates a lack of one or more GluA1-mediated disorders in the subject. In embodiments, In embodiments, the method is a method of detecting PTSD (e.g., GluA1-mediated PTSD) in a subject, and the region of interest is the amygdala of the subject. A GluA1 subunit density or GluA1-containing, GluA2-lacking AMPAR density in the region of interest of the subject greater than the predetermined baseline level may indicate PTSD in the subject. In embodiments, such an evaluation using the detection methods of the present invention may be performed after a subject experiences a trauma and/or before manifestation of symptoms (e.g., observable symptoms). In embodiments, the subject is a subject who experienced a trauma and/or a subject being evaluated for presence of and/or severity of PTSD. In embodiments, evaluation for PTSD may be performed before, during, and/or after treatment, and/or multiple times during the course of a treatment regimen.

In certain embodiments, the methods of the present invention may be performed on a subject who may have a GluA1-mediated disorder (e.g., PTSD) or may be at risk for developing such a disorder. For example, the methods may be performed on a subject who has experienced (e.g., witnessed and/or been a victim of) a traumatic event (e.g., military experiences, accidents, assault, natural disasters, and/or violence, to name a few, which may comprise physical and/or mental traumas). The trauma may be an acute trauma. In embodiments, the trauma may be a chronic trauma comprising a series of milder experiences or events over time. In embodiments, the methods may be performed within a defined period after the traumatic event. For example, in certain embodiments, the radiolabeled composition may be administered (and/or the radiological imaging scan may be performed) within minutes, hours (e.g., at least one hour, 6 hours, 12 hours, to name a few), days (e.g., 1-3 days, to name a few), weeks, months (e.g., 1 month, 2 months, 3 months, 6 months, 9 months, to name a few), or years after the traumatic event. In embodiments, the PTSD detection and/or diagnostic methods described herein may be performed for as long as PTSD symptoms persist. In embodiments, the methods may be performed on a subject having a genetic predisposition to developing a GluA1-mediated disorder, such as PTSD. In embodiments, each patient and/or subject may be given more than one imaging scan (e.g., using the detection methods of the present invention) during his or her lifetime. In embodiments, the detection and/or diagnostic methods of the present invention can be used along with a treatment or treatment regimen to determine subjects requiring treatment, track treatment progress, and/or determine when treatment is no longer needed.

In embodiments, the radiolabeled composition comprises a ligand of GluA1. In such cases, the process may determine GluA1 levels, such as GluA1 subunit density. In embodiments, the radiolabeled composition comprises a ligand of a GluA1-containing, GluA2-lacking AMPAR. In such cases, the process may determine GluA1-containing, GluA2-lacking AMPAR levels and/or density. In embodiments, the radiolabeled composition may be a hybrid or fusion composition to facilitate, for instance, delivery to target cells or efficacy. In embodiments, a hybrid composition may comprise a tissue-specific targeting sequence. For example, in embodiments, the radiolabeled composition may be targeted to the BLA of the subject. In other embodiments, the radiolabeled composition may not be targeted so as to enable the composition to be usable to image a plurality of regions of interest.

In embodiments, the radiological imaging is PET or SPECT imaging. In embodiments, the radiological imaging comprises using another radiation sensing, detection, and/or imaging device. Such a device may be a portable device, such as a handheld electronic device. Accordingly, the radiological imaging may comprise using a portable electronic device to detect radiation levels associated with the radiolabeled composition (e.g., associated with an amount of the radiolabeled composition that has undergone uptake and accumulation in the region of interest, such as the amygdala). In embodiments, such a device may comprise a cellular phone and/or an integrated camera. The radiation sensing device may have installed thereon on non-transitory computer-readable memory, or otherwise may be operable with, particularly programmed software, which can evaluate detected radiation levels, e.g., to provide an indication or notification of such levels and/or to provide an indication or notification that such levels exceed a preprogrammed baseline level. Such software may comprise an installable application, such as a downloadable or an uploadable application.

In embodiments, determining or quantifying GluA1 subunit density and/or levels of GluA1-containing, GluA2-lacking AMPAR density and/or levels in the region of interest (e.g., brain or one or more particular regions of the brain) of the subject can comprise determining or quantifying an amount of the radiolabeled composition in the region of interest after administration. In embodiments, determining or quantifying GluA1 subunit density or GluA1-containing, GluA2-lacking AMPAR density in the region of interest of the subject can comprise detecting, determining, quantifying, visualizing, and/or estimating radioactive emissions of the radiolabeled composition in the region of interest after administration. In embodiments, the radioactive emissions correspond to binding and localization of the radiolabeled composition in the region of interest. Detectable and/or measurable radioactive emissions may thus provide a proxy for detecting and/or measuring GluA1 itself or GluA1-containing, GluA2-lacking AMPARs, via receptor binding of the ligands. For example, increased binding and/or localization of the radiolabeled composition in a region of interest (e.g., the amygdala) would indicate increased GluA1 protein levels, or GluA1-containing, GluA2-lacking AMPAR levels in that region. Accordingly, radioactive emissions may estimate GluA1 levels and/or GluA1-containing/GluA2-lacking AMPAR density, according to the respective ligand used. Radioactive emissions of the administered radiolabeled composition may be detected, quantified visualized, and/or estimated following an uptake period of time after or during which the composition can accumulate and/or bind to its target GluA1 protein or GluA1-containing, GluA2-lacking AMPARs, e.g., in the region of interest. Such radioactive emissions from the radiolabeled composition or a portion thereof (e.g., the portion that bound to targets in an area of interest and/or area to be imaged) may be detected by a special-purpose camera or imaging device that can produce pictures, provide molecular information, and/or provide indications of detected radiation levels, e.g., indicating the locations of such detected radiation. This special-purpose camera or imaging device may image the whole body, whole brain, or just one or more regions of the brain that are of interest.

In embodiments, the method may further comprise comparing the radiolabeled composition in the region of interest after administration to a control amount. In embodiments, the method may further comprise comparing the radioactive emissions of the radiolabeled composition in the region of interest after administration to a control (e.g., a control image, a control amount or control level or control density, or a control density representation, to name a few). In embodiments, the method may comprise comparing receptor density associated with the radioactive emissions to a control receptor density. In embodiments, a control density representation may comprise a visual representation of a control amount of GluA1 or of GluA1-containing, GluA2-lacking AMPARs in the region of interest which may be a particular subject's region of interest (e.g., with a visual representation of the control amount overlaid thereon) or an artistic rendering of a region of interest with the control amount. Such a visual representation may be generated (e.g., by particularly programmed software) and/or provided to technicians, doctors, and/or other personnel, and/or used for diagnostic purposes.

The control amount and/or the control receptor density may be a predetermined baseline level, which baseline may be determined as described herein. In embodiments, the baseline level may be associated with a particular radiolabeled composition. In embodiments, the control amount may be an amount or estimation of radioactive emissions from a region of interest, such as a brain or one or more particular regions of the brain, e.g., an amygdala. In embodiments, the control amount may be an amount, level, and/or density of GluA1 protein or of GluA1-containing, GluA2-lacking AMPARs. In embodiments, the method may further comprise comparing the emissions of the radiolabeled composition in the region of interest after administration to a reference brain region or other organ with a known or approximately known GluA1 amount or GluA1-containing, GluA2-lacking AMPAR amount. In embodiments, the method may comprise using an uptake value, such as a standardized uptake value and/or a fractional uptake value, to determine levels of GluA1, either alone as a subunit protein or in GluA1-containing, GluA2-lacking calcium permeable AMPAR complexes.

A method of detecting GluA1, either itself (e.g., detecting the GluA1 protein subunit itself, whether isolated or not isolated from other compositions) in a region of interest of a subject or as part of a GluA1-containing, GluA2-lacking AMPAR complex in the region of interest of the subject is provided. In embodiments, the method is a method of detecting GluA1 protein levels, or a method of detecting GluA1-containing, GluA2-lacking AMPAR levels, in the region of interest of the subject. In embodiments, the region of interest may comprise one or more regions of the subject, such as one or more brain regions. In embodiments, the method may determine and/or detect elevated GluA1 levels and/or that GluA1 levels are not elevated (e.g., at or around baseline or below baseline). In embodiments, the method may determine and/or detect decreased GluA1 levels and/or that GluA1 levels are not decreased (e.g., at or around baseline or below baseline).

The method comprises administering to the subject a first amount of a radiolabeled composition (e.g., comprising at least one ligand of GluA1 labeled with a radioisotope or comprising at least one ligand of a GluA1-containing, GluA2-lacking AMPAR labeled with a radioisotope); creating at least one image of at least the region of interest of the subject (e.g., imaging a brain while the region of interest is a portion thereof, such as an amygdala) using radiological imaging (e.g., PET or SPECT); and determining or quantifying from the at least one image a GluA1 level (e.g., GluA1 subunit density) or a GluA1-containing, GluA2-lacking AMPAR level (e.g., density level) in the region of interest of the subject based at least in part upon an amount of the radiolabeled composition (e.g., an amount of selective uptake and accumulation of the radiolabeled composition in the region of interest) detected and/or detectable in the at least one image and/or an amount of radioactivity or radioactive emissions (e.g., from the first amount of the radiolabeled composition) detected or displayed in the at least one image. In embodiments, the GluA1 subunit density or the GluA1-containing, GluA2-lacking AMPAR density in the region of interest of the subject may be indicative of GluA1 protein levels, or GluA1-containing, GluA2-lacking AMPAR levels, respectively, in the region of interest of the subject. Accordingly, in embodiments, the method comprises determining or quantifying from the at least one image a level of radioactive emissions in the region of interest as a proxy for determining a GluA1 subunit density or a GluA1-containing, GluA2-lacking AMPAR density in the region of interest of the subject. In embodiments, the at least one image of the brain may be created between 15 minutes and 3 hours following administration of the radiolabeled composition.

In embodiments, the foregoing method may be a method of detecting a GluA1-mediated disorder in a subject. In embodiments, the method may further comprise comparing the density so determined or quantified with a predetermined baseline level, wherein a density different than the predetermined baseline level indicates a GluA1-mediated disorder in the subject. Accordingly, the method may comprise determining whether the GluA1 subunit density or the GluA1-containing, GluA2-lacking AMPAR density in the region of interest exceeds or is less than a predetermined baseline level.

In embodiments, the method is a method of detecting PTSD (e.g., GluA1-mediated PTSD) in the subject, and the region of interest is the amygdala. In embodiments, the method may further comprise comparing the GluA1 subunit density or the GluA1-containing, GluA2-lacking AMPAR density with a predetermined baseline level, wherein a density greater than the predetermined baseline level indicates PTSD (e.g., GluA1-mediated PTSD) in the subject.

In embodiments, the radiolabeled compositions provided by the present invention can each serve as an imaging agent composition, e.g., to enable and/or to facilitate radiological imaging, such as via PET or SPECT. Radiological imaging procedures, such as PET scans, can be performed using any method known to the skilled artisan. In embodiments, the amount of the radiolabeled composition detected and/or detectable in the at least one image comprises an amount of radioactive emissions detected, e.g., detected in the amygdala. Accordingly, the methods of detection provided herein may comprise determining or quantifying from the at least one image a GluA1 level or GluA1-containing, GluA2-lacking AMPAR level in the brain or one or more particular brain regions of the subject based at least in part upon a detected amount of radioactive emissions, e.g., from the one or more regions of interest. The radioactive emissions correspond to a portion of the first amount of the radiolabeled composition that has undergone selective uptake and accumulation, e.g., by binding to the GluA1 protein itself or to GluA1-containing, GluA2-lacking AMPARs, respectively.

The present invention provides a method of detecting or determining presence of a GluA1-mediated disorder in a subject comprising administering to the subject a first amount of a radiolabeled composition effective as a tracer for radiological imaging; subjecting a brain of the subject to radiological imaging capable of detecting radioactive emissions from the radiolabeled composition; and determining or quantifying, based at least in part upon the radiological imaging (e.g., by detecting radioactive emissions), radioactive emissions corresponding to a second amount of the radiolabeled composition that is in the region of interest after administration of the first amount (e.g., after a period of uptake and biodistribution), wherein a difference in binding and localization of the radiolabeled composition in the region of interest compared to a normal subject without the GluA1-mediated disorder is indicative of the GluA1-mediated disorder. In embodiments, the binding and localization of the radiolabeled composition in the region of interest of the subject corresponds to GluA1 subunit levels or GluA1-containing, GluA2-lacking AMPAR levels in the region of interest of the subject. In embodiments, the GluA1-mediated disorder is PTSD, the region of interest is the amygdala, and increased binding and localization of the radiolabeled composition in the amygdala compared to a baseline for the subject without PTSD (or other subjects without PTSD) is indicative of PTSD in the subject.

In embodiments, the methods of detection provided herein may further comprise determining whether GluA1, either alone as a subunit protein or as part of a GluA1-containing, GluA2-lacking AMPAR complex in a region of interest (e.g., the amygdala) exceeds a predetermined baseline level or is less than a baseline level, which baseline may be determined as described herein. In embodiments, the methods may further comprise providing a diagnosis for a psychological disorder (e.g., PTSD) based at least in part upon the determination of whether GluA1 levels (e.g., GluA1 subunit density) or GluA1-containing, GluA2-lacking AMPAR levels (e.g., density) in a region of interest (e.g., the amygdala) differ from (e.g., exceed) the predetermined baseline level by at least a threshold amount. In embodiments, the threshold amount is zero, and the baseline is a GluA1-containing, GluA2-lacking AMPAR level over which the subject has elevated levels of GluA1-containing, GluA2-lacking AMPARs corresponding to presence of a disorder such as PTSD. In embodiments, the threshold amount may be a percentage amount greater than a baseline level of subjects without the disorder (e.g., non-PTSD subjects), which percentage amount may fall in the range of 5-10%, 5-15%, or 5-25%, to name a few. In embodiments, the threshold amount may be a numeric amount of GluA1-containing, GluA2-lacking AMPARs greater than a baseline level of subjects without the disorder (e.g., non-PTSD subjects). In embodiments, an AMPAR level below a baseline level and/or below a baseline level by at least a threshold amount may indicate a disorder. The threshold for indicating, determining, and/or diagnosing a disorder, e.g., PTSD, may be determined by comparison (e.g., statistical analysis) of measured levels of GluA1-containing, GluA2-lacking AMPAR in respective regions of interest (e.g., respective amygdalae) of healthy control subjects and of subjects suffering from the disorder. In embodiments, a plurality of baseline levels may correspond to differing degrees of PTSD or a subtype thereof, such as a GluA1-mediated PTSD. In embodiments, a plurality of baseline levels may define bands each corresponding to different probabilities of having a GluA1-mediated psychological disorder and/or each corresponding to a different degree of such a disorder.

In embodiments, a baseline or predetermined baseline level (e.g., of GluA1 levels or of GluA1-containing, GluA2-lacking AMPAR levels (e.g., density)) may be determined by performing the imaging detection process on a plurality of subjects known not to be suffering from a GluA1-mediated disorder; determining respective GluA1 levels or GluA1-containing, GluA2-lacking AMPAR levels in the brain or one or more particular regions thereof in each of the plurality of subjects; and computing as the predetermined baseline level a normalized average of the respective GluA1 levels or GluA1-containing, GluA2-lacking AMPAR levels in the brain or one or more particular regions thereof in each of the plurality of subjects. In embodiments, the disorder is PTSD, and the region of the brain is the amygdala, wherein the method comprises determining respective amygdalar GluA1 levels or GluA1-containing, GluA2-lacking AMPAR levels.

In embodiments, the predetermined baseline level (e.g., of GluA1 levels (e.g., density) or of GluA1-containing, GluA2-lacking AMPAR levels (e.g., density)) may be determined by performing the imaging detection process on a first plurality of subjects known not to be suffering from a GluA1-mediated disorder (e.g., healthy subjects with respect to the disorder); determining first respective GluA1 density or GluA1-containing, GluA2-lacking AMPAR density in respective brains or one or more regions thereof in each of the first plurality of subjects; computing a first normalized average of the first respective GluA1 density or GluA1-containing, GluA2-lacking AMPAR density; performing the imaging detection process on a second plurality of subjects known to be suffering from the GluA1-mediated disorder; determining second respective GluA1 density or GluA1-containing, GluA2-lacking AMPAR density in respective brains or one or more regions thereof in each of the second plurality of subjects; computing a second normalized average of the second respective GluA1 density or GluA1-containing, GluA2-lacking AMPAR density; and determining as the predetermined baseline level a GluA1 density or GluA1-containing, GluA2-lacking AMPAR density in the brain or one or more regions thereof based at least in part upon the first normalized average and the second normalized average. In embodiments, the GluA1-mediated disorder is PTSD, and the brain region of interest is the amygdala, wherein the method comprises determining amygdalar GluA1 density or GluA1-containing, GluA2-lacking AMPAR density. Determining the baseline may comprise performing one or more study replications and/or comparing across many subjects, e.g., using statistical analyses.

In embodiments, the baseline may be an individualized baseline based at least in part upon a level, amount, and/or density of GluA1 or GluA1-containing, GluA2-lacking AMPARs in one or more regions of the same brain (e.g., reference regions) other than the one or more regions of interest. For example, for PTSD the brain region of interest may be the amygdala, and the one or more other regions of the brain for the baseline determination may be the cerebellum, e.g., of the same brain. Determining such levels in the one or more other regions of the brain may comprise use of the nuclear imaging techniques described herein, wherein the one or more other brain regions are imaged instead of or in addition to the region of interest.

Accordingly, a process for determining an individualized baseline for a subject may comprise administering to the subject a first amount of a radiolabeled composition (e.g., comprising a ligand of GluA1 or a ligand of a GluA1-containing, GluA2-lacking AMPAR) effective for detection of the radiolabeled composition in one or more reference regions (e.g., a cerebellum) of a brain of the subject using radiological imaging; and determining or quantifying, by the radiological imaging of the radiolabeled composition in the one or more reference regions of the brain of the subject, GluA1 subunit density or GluA1-containing, GluA2-lacking AMPAR density in the one or more reference regions of the brain of the subject. In embodiments, the one or more reference regions are distinct from one or more regions of interest for a respective GluA1-implicated disorder. In embodiments, an average baseline level may be computed by averaging the levels detected and/or quantified in different brain regions.

In embodiments, determining an individualized baseline by determining levels of GluA1 or GluA1-containing, GluA2-lacking AMPARs in one or more reference regions of the brain other than the regions of interest for one or more particular GluA1-mediated disorders may be performed after development in the subject of one or more GluA1-mediated disorders since the method relies upon analysis of brain regions where GluA1 levels are known not to impact the respective disorders. The method may also be performed prior to development of the one or more GluA1-mediated disorders and/or prior to exposure to and/or experiencing of events or conditions that may lead to development of such GluA1-implicated disorders.

In embodiments, the one or more reference regions of the brain may be regions of interest for a respective GluA1-implicated disorder, and the individualized baseline may be determined prior to development of a respective GluA1-implicated disorder and/or prior to exposure to and/or experiencing of events or conditions that may lead to development of a GluA1-implicated disorder. For example, for assessing a subject for PTSD, an individualized baseline may be determined prior to a subject's experiencing a trauma, such as before a soldier deploys to a combat zone. Such a baseline may be determined by detecting GluA1 levels or GluA1-containing, GluA2-lacking AMPAR levels in the amygdala of the brain of the subject and/or in other brain regions.

In embodiments, the present invention provides a software product designed to run on one or more computer processors and particularly programmed on non-transitory computer-readable memory to evaluate and/or determine whether a GluA1 subunit density or GluA1-containing, GluA2-lacking AMPAR density determined in a region of interest through the nuclear imaging methods of the present invention exceeds or is less than a predetermined baseline level. The software may be programmed to stratify results based on degrees of severity and/or amount or percentages of difference from the baseline level. The software may be programmed to render and/or display on an output device (e.g., a display screen or a printer) and/or to send electronically to one or more other user electronic devices (e.g., computers or mobile phones) textual and/or graphical representations of the results and/or the data.

In embodiments, the methods described herein for detecting GluA1, GluA1-containing, GluA2-lacking AMPAR complexes, and/or GluA1-mediated disorders in a subject may be performed for a living subject and/or in a subject post-mortem. Accordingly, the radiological imaging techniques described herein provide a significant improvement over prior art techniques that could only be performed post-mortem to detect GluA1 levels or GluA1-containing, GluA2-lacking AMPAR levels. Methods performed post-mortem may comprise administering the radiolabeled composition directly to a region of interest, such as a brain region of interest (e.g., the amygdala), and determining tissue localization of the radiolabeled composition, such as with autoradiography. Such methods performed on a non-living subject may further comprise determining GluA1 or GluA1-containing AMPAR density in the brain or in one or more particular brain regions of the subject using autoradiography with the radiolabeled composition.

The present invention provides a method of treating a GluA1-mediated disorder in a subject (e.g., a living subject) comprising receiving information indicating a detection of non-baseline levels (e.g., elevated or reduced levels) of GluA1, either alone as a subunit protein or in GluA1-containing, GluA2-lacking calcium permeable AMPAR complexes, in a region of interest of the subject, wherein the detection has been obtained by administering to the subject an amount of a radiolabeled composition effective to detect the radiolabeled composition (e.g., by detecting radioactive emissions from the radiolabeled composition) in the region of interest of the subject using radiological imaging (e.g., PET or SPECT); determining or quantifying GluA1 levels or GluA1-containing, GluA2-lacking AMPAR levels in the region of interest of the subject (e.g., by detecting from the region of interest radioactive emissions from a portion of the amount of the radiolabeled composition that has bound to GluA1 subprotein or to GluA1-containing, GluA2-lacking AMPARs); and determining that the GluA1 levels or the GluA1-containing, GluA2-lacking AMPAR levels differ from (e.g., exceed or are below) a predetermined baseline level. The method of treating further comprises administering to the subject an amount of a treatment composition effective to treat the disorder. In embodiments, the method may comprise comparing the radiolabeled composition in the region of interest after administration (e.g., or emitted radiation therefrom) to a control amount, which may be a predetermined baseline level. In embodiments, the method may comprise comparing receptor density associated with the radioactive emissions to a control receptor density, which may be a predetermined baseline level.

In embodiments, the GluA1-mediated disorder is PTSD (e.g., GluA1-mediated PTSD), and the region of interest is the amygdala. Elevated levels of GluA1 levels or GluA1-containing, GluA2-lacking AMPAR levels in the region of interest of the subject compared to a baseline level may indicate PTSD in the subject. Accordingly, a method of treating PTSD (e.g., GluA1-mediated PTSD) in a subject is provided. The method comprises receiving information indicating a detection of elevated levels of GluA1, either alone as a subunit protein or in GluA1-containing, GluA2-lacking calcium permeable AMPAR complexes in a region of interest that is an amygdala of the subject, wherein the detection has been obtained by administering to the subject an amount of a radiolabeled composition comprising at least one radiolabeled ligand of GluA1 or comprising at least one radiolabeled ligand of a GluA1-containing, GluA2-lacking AMPAR, the amount of the radiolabeled composition effective to detect the radiolabeled composition in the amygdala of the subject using radiological imaging (e.g., PET or SPECT); determining or quantifying GluA1 levels or GluA1-containing, GluA2-lacking AMPAR levels in the amygdala of the subject; and determining that the GluA1 levels or the GluA1-containing, GluA2-lacking AMPAR levels exceed a predetermined baseline level, which may be determined as described herein. The method further comprises administering to the subject an amount of a treatment composition effective to treat PTSD. In embodiments, the treatment composition may be capable of crossing a blood-brain barrier of the subject, e.g., to enter the region of interest.

In embodiments, the administered treatment composition (e.g., the respective amount of the treatment composition) may be effective to reduce GluA1 levels or expression levels (e.g., thereby blocking the formation of functional GluA1-containing AMPARs) or to reduce GluA1-containing, GluA2-lacking AMPAR expression levels in the region of interest (e.g., amygdala) of a subject. In embodiments, the administered treatment composition may be effective to block the function of formed GluA1 protein or GluA1-containing, GluA2-lacking AMPARs in the region of interest of the subject. In embodiments, such a treatment composition effective to alter GluA1 levels or expression levels may be selected from the group consisting of a nucleic acid, an antisense oligonucleotide, a ribozyme, a peptide, a small molecule, an inhibitor of GluA1 expression or synthesis, an aptamer, and a peptidomimetic.

In embodiments, the treatment composition comprises a GluA1-containing, GluA2-lacking AMPAR ligand. In embodiments, the treatment composition comprises an inhibitor of calcium permeable AMPAR function. In embodiments, the respective amount of the treatment composition is effective to inhibit receptor function of GluA1-containing, GluA2-lacking AMPARs in the region of interest (e.g., amygdala) of the subject. In embodiments, such a treatment composition may be selected from the group consisting of a peptide, a small molecule, an antagonist, an inhibitor, an allosteric modulator, and a peptidomimetic. In embodiments, such a treatment composition may alleviate one or more symptoms of PTSD.

In embodiments, the treatment composition, depending on the disorder being treated, may be effective to increase GluA1 levels or expression levels, either alone as a subunit protein or in AMPAR complexes, in the region of interest, or to activate GluA1-containing, GluA2-lacking AMPARs and/or enhance (e.g., increase) receptor function of GluA1-containing, GluA2-lacking AMPARs in the region of interest.

Accordingly, the present invention provides a composition effective to reduce GluA1 expression levels or GluA1-containing, GluA2-lacking AMPAR expression levels the amygdala of a subject or effective to block or inhibit receptor function of GluA1-containing, GluA2-lacking AMPAR in the amygdala of a subject for use in the treatment of a patient with a GluA1-mediated disorder (e.g., PTSD), wherein the patient is selected by receiving information indicating detection of non-baseline (e.g., elevated or diminished) levels of GluA1, either alone as a subunit protein or in GluA1-containing, GluA2-lacking calcium permeable AMPAR complexes in a region of interest (e.g., an amygdala) of the subject, wherein the detection has been obtained by administering to the subject an amount of a radiolabeled composition comprising at least one radiolabeled ligand of GluA1 or comprising at least one radiolabeled ligand of a GluA1-containing, GluA2-lacking AMPAR, the amount of the radiolabeled composition effective to detect the radiolabeled composition in the region of interest of the subject using radiological imaging (e.g., PET or SPECT); determining or quantifying GluA1 levels or GluA1-containing, GluA2-lacking AMPAR levels in the region of interest of the subject; and☐ determining that the GluA1 levels or the GluA1-containing, GluA2-lacking AMPAR levels exceed or are less than a predetermined baseline level. In embodiments, the GluA1-mediated disorder is PTSD, the region of interest is the amygdala, and the GluA1 levels or the GluA1-containing, GluA2-lacking AMPAR levels exceed the baseline levels.

In embodiments, the radiolabeled composition is a radiolabeled detector or otherwise may have any of the properties and/or structures as described herein with respect to radiolabeled compositions, detectors, tracers, and/or imaging agents. The radiolabeled composition may comprise a saline and/or ethanol solution.

In embodiments of the present invention provided herein, the radiolabeled composition may be administered to the subject via injection into the bloodstream (e.g., intravenous injection and/or intravenous drip), via injection into tissue and/or an organ, via enema, orally (e.g., in pill, tablet, or liquid form), via inhalation, and/or via a nasal spray, in a manner effective to enter the region of interest of the subject.

In embodiments, the radiolabeled composition may be administered along with a liver-mediated drug metabolism inhibitor, such as disulfiram, miconazole, or another broad-spectrum cytochrome P450 (CYP) inhibitor. Such an inhibitor may prevent or delay metabolism of the radiolabeled composition, e.g., within the liver, by targeting the CYP enzyme class, which can facilitate biodistribution of the radiolabeled composition and a stronger signal in the region of interest, e.g., the amygdala or another brain region.

In embodiments, the amount of the radiolabeled composition administered to the subject (e.g., the first amount) comprises a mass dose of the radiolabeled composition in a range of 0.0001 pg to 1 ng per kg of body weight of the subject. In embodiments, such a mass dose may fall in the range 0.01-2 pg/kg. In embodiments, an amount of radioactivity associated with the amount of the radiolabeled composition administered to the subject falls in a range of 1 to 2000 MBq. In embodiments, such a radioactivity level may fall in a range of 1-150 MBq, 100-250 MBq, 200-300 MBq, 150-370 MBq, 300-400 MBq, or 400-2000 MBq, to name a few. In some embodiments an effective radiation dose equivalent associated with the amount of the radiolabeled composition administered to the subject falls in a range of 1 to 100 μSv, which is linearly related to radioactivity. In embodiments, the radiation doses may fall in a range of 1-12 μSv, 10-25 μSv, 20-30 μSv, 30-40 μSv, to name a few.

Administration of the radiolabeled composition (and/or a solution thereof) in accordance with the present invention may occur in one bolus administered some time (e.g., an uptake period) before the detection and/or imaging takes place. However, in embodiments, the administration of the agents of the invention may be essentially continuous over a preselected period of time, may comprise a series of spaced doses, or may comprise a singly administered dose, depending on factors known to skilled practitioners. Both local and systemic administration are contemplated. The amount administered may vary depending on various factors including, but not limited to, the composition chosen, a particular target being evaluated (e.g., GluA1 protein or GluA1-containing, GluA2-lacking AMPARs), a particular disease being evaluated (e.g., PTSD, anxiety, to name a few), the weight, the physical condition, and/or the age of the subject. Such factors can be determined by a clinician employing animal models or other test systems which are well known to the art. An effective amount of a composition for use in an imaging diagnostic procedure may be an amount sufficient to be detected by the imaging procedure, e.g., PET technique via detection of radioactive emissions, or may be an amount sufficient to bind to a target receptor.

When the radiolabeled ligands of the invention are prepared for administration, they may be combined with a pharmaceutically acceptable carrier, diluent, or excipient to form a pharmaceutical formulation, or unit dosage form.

In embodiments, an uptake period during which the radiolabeled composition travels through a body of a subject may be in the range of 5 to 100 minutes, 45 to 60 minutes, or 45 to 90 minutes, to name a few. Accordingly, an uptake period may be 5 minutes, 15 minutes, 30 minutes, 45 minutes, 50 minutes, 60 minutes, 80 minutes, 85 minutes, or 90 minutes, to name a few. An image acquisition time or a scan duration for a radiological imaging procedure (e.g., a PET scan or a SPECT scan) may be in the ranges of 5 to 45 minutes, 15 to 60 minutes, 30 to 60 minutes, or 30 to 90 minutes, to name a few, such as scan durations of 5 minutes, 10 minutes, 15 minutes, 20 minutes, or 30 minutes, to name a few. In embodiments, shorter scan durations may be performed, such as using a portable radiological sensing and/or imaging device.

EXAMPLES

Introduction

Rodent experiments have suggested a link between upregulation of GluA1 in the amygdala of a subject and PTSD. Using a rodent model of PTSD called SEFL, it has been shown that after a traumatic event, there are enduring increases in GluA1 protein in the BLA (8, 9) (hereby incorporated by reference in their entireties as if fully set forth herein). However, other glutamate receptor subunits, such as the GluA1 subunit of the AMPAR and GluN1 subunit of the NMDAR, do not show any long-term changes (FIGS. 2A-D).

Figure 2A:
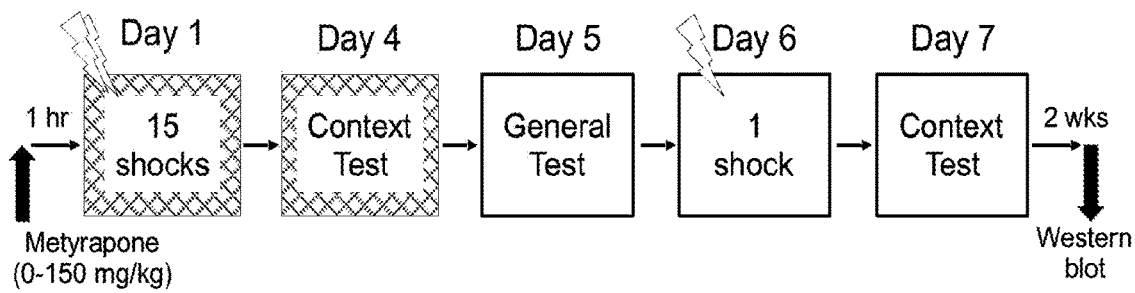
FIG. 2A illustrates an experimental design for Stress-Enhanced Fear Learning (SEFL), a rodent model of PTSD.

FIG. 2A illustrates an experimental design using SEFL (10, 11). Protein levels were measured using Western blot, an analytical technique to detect specific proteins in tissue samples.

FIG. 2B depicts representative Western blot images of GluA1 and a control, GAPDH, from the BLA of stressed and unstressed rats, measured three weeks after the trauma. The graph shows mean GluA1:GAPDH optical density ratios (±SEM). GluA1 protein levels in the BLA were significantly higher in stressed rats than in unstressed rats and metyrapone-treated rats; (**$p<0.01$, two-way analysis of variance (ANOVA), followed by a priori planned comparisons) (8).

FIG. 2C depicts representative Western blot images of GluA2 and GAPDH from the BLA of stressed and unstressed rats, measured three weeks after the trauma. The graph shows mean GluA2:GAPDH optical density ratios (±SEM). Neither stress nor metyrapone had an effect on GluA2 levels (8).

FIG. 2D depicts representative Western blot images of GluN1 and GAPDH from the BLA of stressed and unstressed rats, measured three weeks after the trauma. The graph shows mean GluN1:GAPDH optical density ratios (±SEM). Neither stress nor metyrapone had an effect on GluN1 levels (8).

Figure 3A:
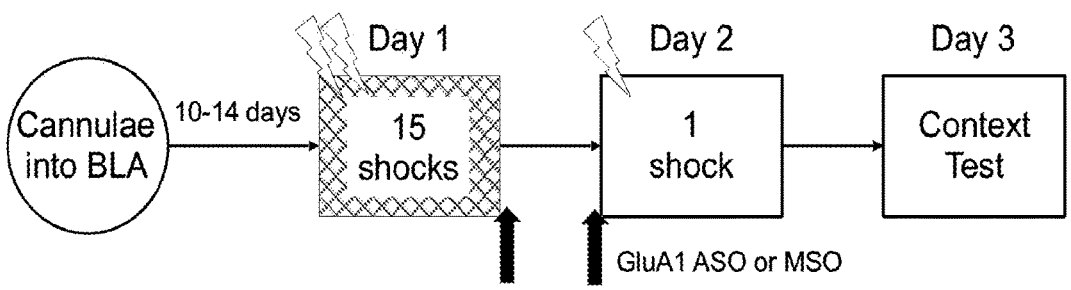
FIG. 3A illustrates an abbreviated SEFL experimental design.
Figure 3B:
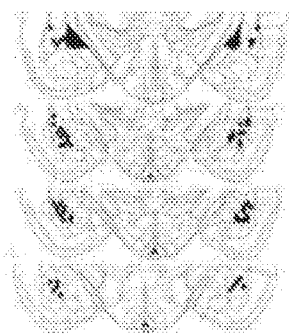
FIG. 3B illustrates cannulae placement into the basolateral amygdala (BLA) of rodents.
Figure 3C:
FIGS. 3C-E depict the results of example experiments demonstrating that intra-BLA infusions of GluA1 antisense oligonucleotide (ASO) after the 15-shock stressor reverse the SEFL. Delivering GluA1 ASO post-trauma significantly decreased GluA1 protein levels in stressed rats. Missense oligonucleotide (MSO) control infusions still conferred high level of GluA1 protein, as determined by Western blotting (FIGS. 3C-D) GluA1 ASO post-trauma also prevented the sensitized fear (i.e., freezing) typically observed in novel Context B after just a mild shock (labeled in the graph as the conditioning context) after receiving a trauma in context A (FIG. 3E).
Figure 3D:
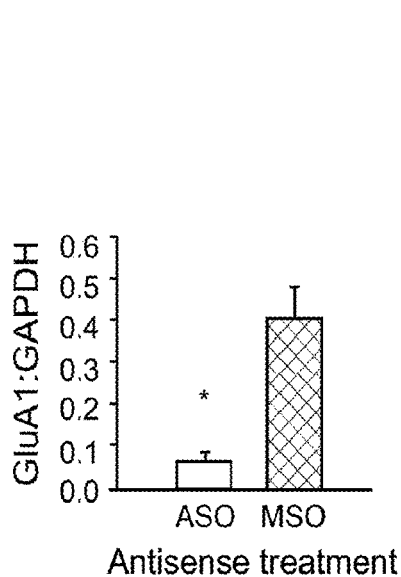
Figure 3E:
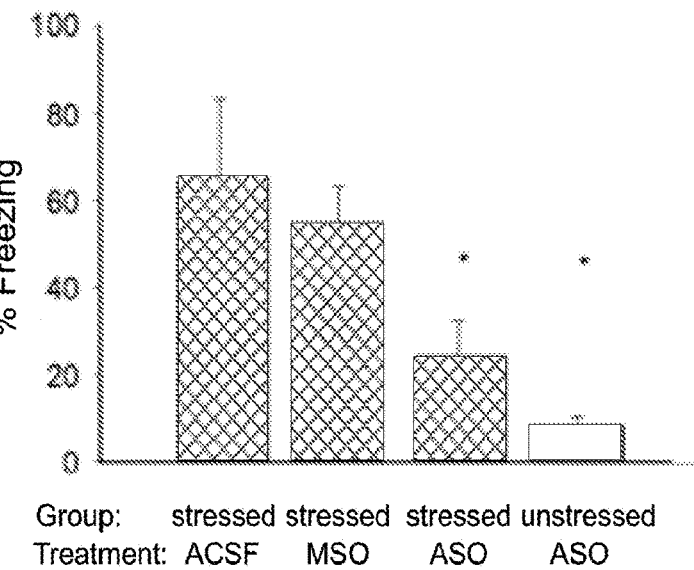

Because GluA1 increases are observed weeks after the trauma, post-trauma GluA1 ASO infusions directly into the BLA prevented sensitized fear responses usually observed in SEFL (FIGS. 3A-E) (8). FIG. 3A illustrates the experimental design, and FIG. 3B shows the cannulae placement. FIG. 3C depicts representative Western blot images of GluA1 and GAPDH from the BLA of stressed/MSO and stressed/ASO rats. FIG. 3D depicts mean GluA1:GAPDH optical density ratios(±SEM) from the BLA of stressed/MSO and stressed/ASO rats. ASO significantly lowers GluA1 levels in the BLA when delivered after the trauma compared with MSO (*$p<0.05$, one-way ANOVA). FIG. 3E depicts mean(±SEM) percent freezing in Context B on Day 3. GluA1 ASO significantly reduces conditional freezing compared with stressed controls (i.e., those infused with artificial cerebrospinal fluid (ACSF) or MSO) when delivered into the BLA post-trauma to unstressed levels (* $p<0.05$, one-way ANOVA followed by planned comparisons).

Figure 4A:
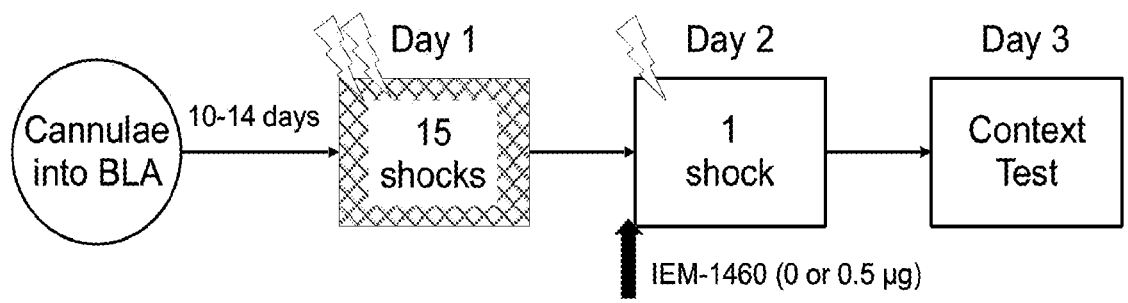
FIG. 4A illustrates a SEFL experimental design.
Figure 4B:
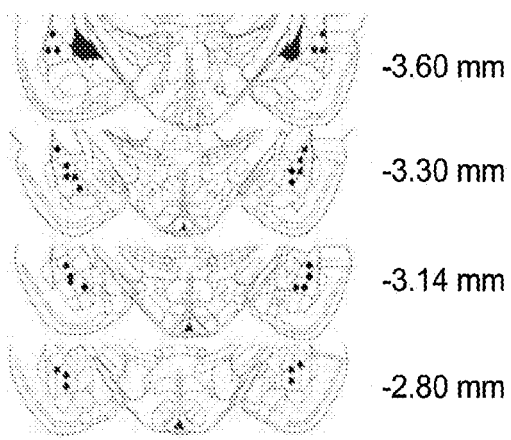
FIG. 4B illustrates cannulae placement verification in the BLA.
Figure 4C:
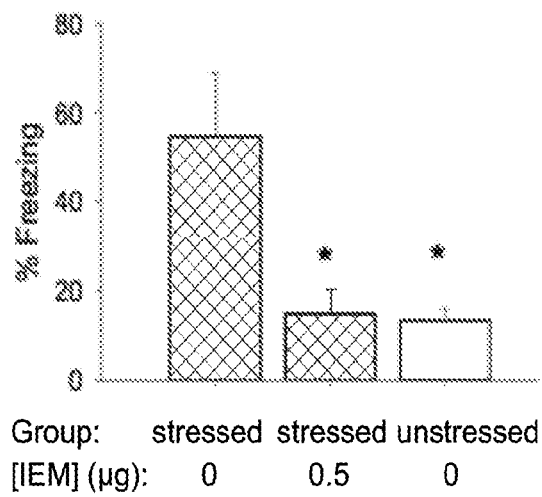
FIG. 4C depicts the results of example experiments demonstrating that intra-BLA infusions of IEM-1460, a selective GluA2-lacking AMPAR antagonist, after the 15-shock stressor attenuate SEFL. Blocking GluA2-lacking AMPARs in the amygdala post-trauma block the sensitized fear (i.e., freezing) typically observed in novel Context B after just a mild shock (labeled in the graph as the conditioning context) after receiving a trauma in Context A.

Similar results were observed using IEM-1460, a GluA2-lacking, GluA1-containing AMPAR antagonist, suggesting that the GluA1 subunit increase also increased viable GluA1-containing AMPARs, which can be bound to and acted upon by a ligand, either endogenous glutamate, its native excitatory neurotransmitter that activates these receptors, or an exogenous drug to either activate or inhibit activity of these receptors (FIGS. 4A-C) (8). FIG. 4A depicts a SEFL experimental design, and FIG. 4B shows cannulae placement verification. FIG. 4C depicts mean freezing (±SEM) in Context B on Day 3. IEM-1460 infused post-trauma significantly reduces freezing in Context B compared with stressed rats infused with ACSF and unstressed controls (* $p<0.05$, one-way ANOVA, followed by a priori planned comparisons) (8).

This work discussed hereinabove was conducted in rodents using Western blotting techniques to detect glutamate receptor protein levels. Western blotting to detect specific proteins in humans is not viable in living subjects; it requires using post-mortem tissue and artificial antibodies to react with the target protein in this tissue. The present invention provides alternative methods to detect GluA1 protein levels utilizing nuclear imaging, which can be performed in live human patients, as well as post-mortem. Instead of designing antibodies to react with the target protein in the tissue sample, nuclear imaging requires injecting a radioisotope with specificity to the protein that will also be able to penetrate the region of interest in awake patients. In particular for the present invention, nuclear imaging can be effected by radiolabeling a ligand of GluA1 or of GluA1-containing, GluA2-lacking AMPARs, such as those used in the outlined studies. However, while IEM-1460 is a known ligand of GluA1-containing, GluA2-lacking AMPARs, radiolabeling this compound directly with [$^{18}$F] in a manner that preserves its ability to bind to GluA1 is not feasible.

Difficulty of Radiolabeling

Figure 1B:
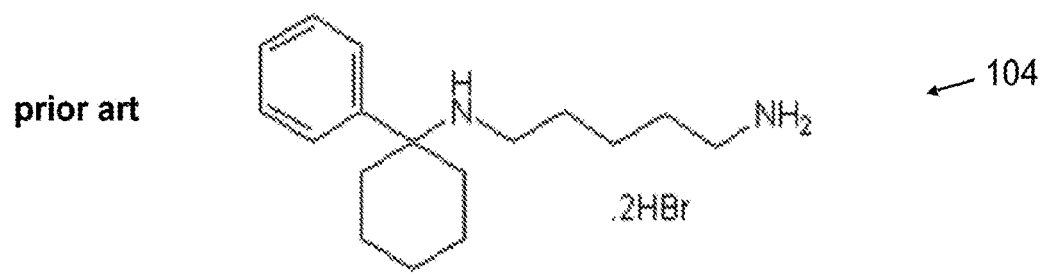

The most direct extrapolation of the example studies would be to radiolabel an already existing and commercially available drug that binds to GluA1-containing/GluA2-lacking AMPARs, such as IEM-1460 (N,N,H,-Trimethyl-5-[(tricyclo[3.3.1.13,7]dec-1-ylmethyl) amino]-1-pentanaminiumbromide hydrobromide, depicted in FIG. 1A), IEM-1925 (N-(1-Phenylcyclohexyl)-1,5-pentanediamine dihydrobromide, depicted in FIG. 1B), or other adamantane or phenylcyclohexyl derivatives. These classes of ligands have never before been radiolabeled.

Figure 5:
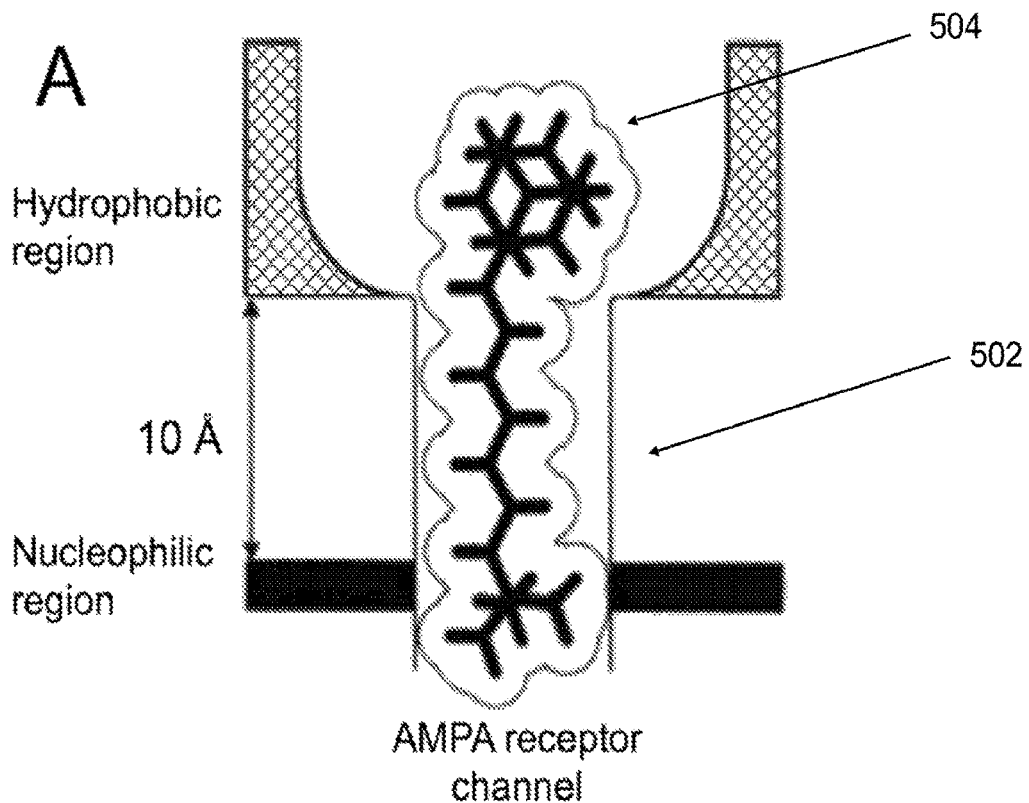
FIG. 5 illustrates a topographical model of channel binding sites in AMPARs. Hydrophobic and nucleophilic regions in the receptor are separated by approximately 10 A. Therefore, only compounds possessing a 'head and tail' structure such as IEM-1460 can block the channel.

Radiolabeling such a ligand is complicated by the necessity to add the radioisotope at a particular location of the structure so as not to interfere with and/or prevent binding. FIG. 5 illustrates exemplary AMPAR channel binding sites (12). Ligands of AMPARs have similar 'head and tail' structures with two primary structural features. The nucleophilic chain 502 is thought to associate with the pore region of ionotropic channels as a cation mimic. The phenylcyclohexyl portion 504 of the molecule is a hydrophobic moiety that fills space in the pore and confers the steric hindrance that prevents cation passage through the pore. According to Bolshakov et al., the nucleophilic chain is important for binding and the chain length is crucial to allow binding to calcium permeable AMPARs (12). Chain length should be approximately 10 Å so that the phenylcyclohexyl, or another hydrophobic group, can interact with the hydrophobic region at the pore of the receptor, while the hydrophilic, nucleophilic group can interact with the nucleophilic region of the receptor.

In embodiments, [$^{11}$C] labeling of these ligands may be possible. However, the [$^{18}$F] radioisotope is preferred to [$^{11}$C] for radiolabeling because its half-life of about 110 minutes is much greater than the approximately 20-minute half-life of [$^{11}$C]. Because of its short half-life, [$^{11}$C] has severely limited clinical usability, requiring an on-site cyclotron to perform the labeling (13). There are some radiometals suitable for clinical use [$^{68}$Ga]) but these are connected to the tracer via large/complex chelators and this would impact the pharmacological properties of the product rendering it unusable for labeling AMPAR ligands.

A strategy for [$^{18}$F] labeling existing GluA1 ligands, such as IEM-1460 or IEM 1925, is not straightforward, as neither compound contains any halogen atoms. Direct fluorination of IEM-1925 would most likely target the nucleophilic amine chain. Interfering with the chain would likely affect channel pharmacology by altering the nitrogen basicity. While a calcium permeable AMPAR ligand with similar structure and function, IEM-1460, has been fluorinated with [$^{19}$F] in the past, the conditions used are not compatible with [$^{18}$F] radiolabeling (14, 15). Moreover, [$^{19}$F] is a stable, non-radioactive isotope and thus not useful for radiological imaging.

Given that direct fluorination of existing GluA1 ligands, such as IEM-1460 or IEM 1925, is unfavorable and/or infeasible in terms of preserving its ability and/or specificity to bind to AMPARs, incorporating [$^{18}$F] into the compound or otherwise creating a radiolabeled ligand of AMPARs and in particular GluA2-lacking AMPARs presents technical challenges.

Method of Manufacture

The radiolabeled compositions of the present invention do not occur naturally. A radiolabeling process was developed to produce a radiolabeled compound that is a ligand of GluA1 or of GluA1-containing, GluA2-lacking AMPARs with a radiolabel (e.g., a radioisotope) in a location that does not prevent binding to the AMPARs. The process requires synthesis of new precursor molecules designed to have the requisite AMPAR binding properties and further designed to radiolabeled with a radioisotope, such as [$^{18}$F]. Each precursor compound is used to synthesize a respective second compound, which is a radiolabeled composition. In embodiments, one or more intermediate molecules between the precursor and the final radiolabeled molecule may be produced. In embodiments, precursor molecules and/or resulting radiolabeled molecule of the present invention are designed to cross the blood-brain barrier, e.g., to enter a brain of a living subject, which may occur through natural biodistribution following administration to the subject.

In the synthesis methods disclosed herein, as depicted in FIGS. 6A-F and FIGS. 7A-E, a modified phenylcyclohexyl derivative compound 602, 603, 606, 610, 614, 618, 702, 706, 710, 714, and 718 respectively, is developed to have an amine tail of the molecule that satisfies a length corresponding to AMPAR binding. The present invention thus provides compounds 602, 603, 606, 610, 614, 618, 702, 706, 710, 714, and 718, having respective structures as depicted. While phenylcyclohexyl derivatives are known generally to bind to calcium permeable AMPARs, the specific binding properties of the precursor compounds 602, 603, 606, 610, 614, 618, 702, 706, 710, 714, and 718 with AMPARs was not previously known. Moreover, phenylcyclohexyl derivatives in general are not common to radiolabel with [$^{18}$F] because there are no halogen-group atoms to replace in the molecule. The precursor compounds 602, 606, 610, 614, 618, 702, 706, 710, 714, and 718 are designed with a radiochemistry leaving group, tosylate, on the far end of the phenyl group (e.g., away from the amine tail) to facilitate novel [$^{18}$F] radiolabeling at this structure instead of at the tail. Precursor compound 603 is designed with a different leaving group that is an iodonium ylide radiochemistry leaving group to facilitate radiolabeling at the phenyl group structure.

A radiofluorination reaction is performed to the precursor compounds 602, 603, 606, 610, 614, 618, 702, 706, 710, 714, and 718 to produce respective radiolabeled compositions 604, 608, 612, 616, 620, 704, 708, 712, 716, and 720, as depicted. For example, as depicted in FIG. 6D, the present invention provides a method of producing a radiolabeled compound comprising performing a radiofluorination reaction on a first compound 610 having the following structure:

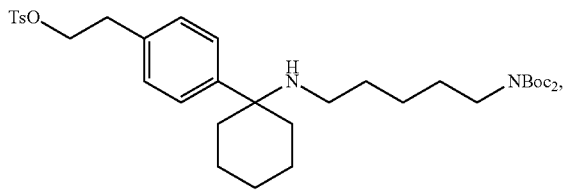

wherein TsO is tosyl and Boc is tert-Butyloxycarbonyl, so as to produce a second compound 612 having the following structure:

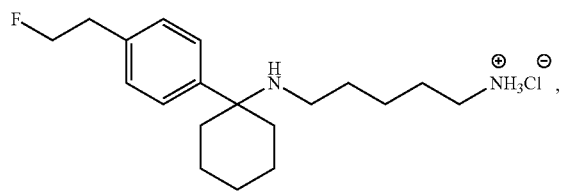

wherein the F is a [$^{18}$F] radioisotope. In embodiments, salts (e.g., pharmaceutically acceptable salts) of compounds 604, 608, 612, 616, and 620 are provided. In embodiments, free base (e.g., respective deprotonated form of an amine) versions of compounds 704, 708, 712, 716, and 720 are provided. In embodiments, the respective compounds may exist in one or more forms, such as free base as well as pharmaceutically acceptable salts. In embodiments, labeling the precursor compounds with a radioisotope can be done using any method known to the skilled artisan.

In embodiments, compound 610 is 5-((1-(4-(2-(4-methylbenzenesulfonyl)ethyl)phenyl)cyclohexyl)amino)pentan-1-N,N-di-tert-butylcarbonate.

In embodiments, compound 612 is 5-((1-(4-(2-fluoroethyl)phenyl)cyclohexyl)amino)pentan-1-aminium.

In embodiments, the present invention provides a method of synthesizing and/or producing a radiolabeled compound. The method comprises synthesizing a [$^{18}$F]fluoride solution comprising [$^{18}$F]fluoride via a (p,n) reaction of [$^{18}$O]water by proton bombardment in a cyclotron. In embodiments to synthesize a compound radiolabeled with a [$^{11}$C] radioisotope, this step may comprise synthesizing [$^{11}$C]carbon dioxide via a (p,n) reaction of [$^{11}$B] by proton bombardment in a cyclotron. The method of producing the radiolabeled compound further comprises extracting and/or trapping the [$^{18}$F]fluoride by passing the [$^{18}$F]fluoride solution through a preconditioned QMA anion exchange cartridge; eluting and/or heating, in a reaction vessel, the extracted [$^{18}$F]fluoride with a first solvent comprising an acetonitrile (MeCN)/water solution containing a phase transfer catalyst (e.g., potassium carbonate (K2CO3) and/or Kryptofix 2.2.2 (KF/K2.2.2); applying a vacuum to the reaction vessel so as to remove the first solvent and leave a dried residue of a [$^{18}$F]KF/K2.2.2 complex; adding, to the reaction vessel, MeCN to re-dissolve the dried residue; evaporating, via application of heat and vacuum to the reaction vessel, so as to remove residual water by azeotropic distillation leaving a second dried residue of [$^{18}$F]KF/K2.2.2 complex; mixing, in a second solvent (e.g., approximately 1 mL of a second solvent, such as MeCN or dimethyl sulfoxide (DMSO)) in the reaction vessel, the second dried residue of the [$^{18}$F]KF/K2.2.2 complex and a compound 610 having the structure shown in FIG. 6D; heating the reaction vessel so as to perform a radiofluorination reaction to produce a radiolabeled compound 612, wherein the F is a [$^{18}$F] radioisotope; and purifying, via radio-High Performance Liquid Chromatography (HPLC), the radiofluorination reaction contents to produce a purified radiolabeled compound. In embodiments, the reaction vessel may comprise one or more different reaction vessels to which reaction contents are added. Heating a reaction vessel heats such reaction contents. In embodiments, these reaction steps may be performed for the other precursor compounds depicted in FIGS. 6A-F and 7A-E to produce the respective radiolabeled structures depicted in those figures.

HPLC is an analytical chemistry technique used to separate, identify, and/or quantify each component in a mixture, which technique is usable here to evaluate and/or ensure purity of the radiolabeled composition. In embodiments, the method may further comprise formulating the purified radiolabeled compound in saline, e.g., to prepare for use in a subject, which may be a mammal, such as a rodent and/or human subject, to name a few. Purification using HPLC may be performed to prepare a solution for administration. In embodiments, the resulting purified fraction may then be reformulated for administration (e.g., injection) either by evaporating off all the solvent and replacing with saline or flowing the pure fraction through a sep-pak cartridge (e.g., C18) to trap the compound. The cartridge can then be washed with water, and the compound may be eluted off the cartridge in a low amount of ethanol. The eluted compound may be diluted with saline, e.g., such that ethanol is <10% v/v. The result may be passed through a sterile filter. In embodiments, quality control testing may be performed.

In embodiments of the present invention, a method of synthesizing a radiolabeled compound comprises obtaining (e.g., producing and/or trapping) an amount of [$^{18}$F]; eluting the [$^{18}$F] with a phase transfer catalyst KF/K2.2.2 so as to produce a solution of [$^{18}$F]KF/K2.2.2 complex; adding a first compound 610 having the structure shown in FIG. 6D to the solution of the [$^{18}$F]KF/K2.2.2 complex (e.g., approximately 1 mL of the solution) so as to perform a radiofluorination reaction to create a second compound 612 having the structure shown in FIG. 6D, wherein the F is a [$^{18}$F] radioisotope. In embodiments, performing the radiofluorination comprises adding heat to the reaction contents and/or to a reaction vessel containing such reaction contents. In embodiments, the method may further comprise purifying the reaction contents from to produce a purified compound radiolabeled with [$^{18}$F]. In embodiments, a subsequent addition of deprotecting agent (e.g., acid) may be added to the reaction vessel and then heated to perform the deprotection reaction to remove Boc groups to form the second compound. In embodiments, purifying the reaction contents can comprise performing radio-HPLC on the product of the radiofluorination reaction. In embodiments, the second compound may be formulated in saline for injection. In embodiments, these reaction steps may be performed for the other precursor compounds depicted in FIGS. 6A-F and 7A-E to produce the respective radiolabeled structures depicted in those figures.

In embodiments, a method of synthesizing a radiolabeled compound comprises isolating [$^{18}$F]; combining the isolated [$^{18}$F] with a phase transfer catalyst (e.g., KF/K2.2.2) to produce a [$^{18}$F] phase transfer buffer; combining that complex with compound 610 having the structure illustrated in FIG. 6D; and adding heat to produce compound 612. In embodiments, these reaction steps may be performed for the other precursor compounds depicted in FIGS. 6A-F and 7A-E to produce the respective radiolabeled structures depicted in those figures.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The nomenclature used herein and the laboratory procedures used in analytical chemistry, radiochemistry, and organic syntheses described herein are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Agonist" refers to a chemical that binds to a receptor and activates the receptor to produce a biological response. The agonist can be endogenous, coming from within the body, or exogenous, coming from outside the body, such as a drug.

"Allosteric modulator" refers to a chemical that indirectly influences or modulates the target receptor. Allosteric modulators bind to a site distinct from that of the agonist binding site and induce a conformational change in the receptor. A positive allosteric modulator induces an amplification of the agonist's effect (i.e., by enhancing binding affinity or functional efficacy of the agonist for the receptor). A negative allosteric modulator decreases the effect of the true ligand but is inactive in the absence of the ligand. A positive allosteric modulator amplifies the effect of the true ligand but is inactive in the absence of the ligand. Allosteric modulators do not compete for the same binding spot as the true ligand.

"Antagonist" refers to a chemical or drug that blocks or dampens agonist-mediated responses rather than provoking a biological response itself upon binding to a receptor. They are sometimes called blockers; examples include calcium channel blockers. In pharmacology, antagonists have affinity but no efficacy for their receptors to which they bind, and binding will disrupt the interaction and inhibit the function of an agonist.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

"Autoradiography" refers to a bioanalytical technique used to visualize the distribution of a substance labeled with radioisotope in an ex vivo biological sample. It is a method by which a radioactive material can be localized within a particular tissue.

"Biomarker" refers to a measurable substance in an organism whose presence is indicative of some phenomenon such as disease, infection, or environmental exposure.

As used herein, "aptamer" refers to a small molecule that can bind specifically to another molecule. Aptamers are typically either polynucleotide- or peptide-based molecules. A polynucleotide aptamer is a DNA or RNA molecule that adopts a highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that binds to specific ligands. Peptide aptamers may be identified and isolated from combinatorial libraries, using methods such as the yeast two-hybrid system.

The terms "diagnose," "diagnosing," and "diagnosis," refer to detecting measures described herein. The methods of "diagnosis" can employ using detection and/or imaging techniques, such as PET scan imaging, on a subject to identify target compounds in target anatomical regions, to identify presence of and/or quantities of target compounds in target anatomical regions, to identify characteristics of target compounds in target anatomical regions, and/or to identify characteristics of target anatomical regions. This can require administration of a composition of the present invention, for example, a subject possibly afflicted with a disease or disorder, in order to detect, identify, determine the severity of, or determine the course of treatment of the disorder or recurring disorder, or in order to prolong the survival of a subject beyond that expected in the absence of such diagnosis.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity or frequency of at least one sign or symptom of the disease or disorder experienced by a patient is reduced.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "isotope" refers to any variant of a particular chemical element which differ in neutron number, although all isotopes of a given element have the same number of protons in each atom. For example, carbon-12, carbon-13 and carbon-14 are three isotopes of the element carbon with mass numbers 12, 13 and 14 respectively. "Radiolabeled" or "Radioactive" as applied to an object, sometimes called "radioisotope" refers to a composition that has excess nuclear energy, making it unstable. This excess energy can either create and emit from the nucleus new radiation (gamma radiation) or a new particle (alpha particle or beta particle), or transfer this excess energy to one of its electrons, causing it to be ejected (conversion electron). During this process, the object is said to undergo radioactive decay. Radioisotopes are used for diagnosis, treatment, and research. Radioactive chemical tracers emitting gamma rays or positrons can provide diagnostic information about internal anatomy and the functioning of specific organs. Radioisotopes can be attached to a ligand in order to determine receptor binding. This is used in some forms of tomography such as PET scanning.

The term "ligand" refers to any substance that forms a complex with a biomolecule, and can serve a biological purpose. In protein-ligand binding, the ligand is usually a molecule which produces a signal by binding to a site on a target protein (usually a receptor). The binding typically results in a change of conformation of the target protein. In DNA-ligand binding studies, the ligand can be a small molecule, ion or protein, that binds to a particular part of the DNA double helix. The relationship between ligand and binding partner is a function of charge, hydrophobicity, and molecular structure. In terms of ligand-receptor binding, the ligand can either be an agonist or antagonist (competitive or non-competitive) of the receptor. "Radiolabeled" or "Radioactive" as applied to an object, sometimes called "radioligand" or "tracer" refers to a biochemical substance (in particular, a ligand that is radiolabeled) that is used for diagnosis or for research-oriented study of the receptor systems of the body. In a neuroimaging application the radioligand can be injected into the pertinent tissue, or infused into the bloodstream and binds to its receptor. In embodiments, the radioligand may be administered orally via swallowing, by inhalation, by injection (intravenous), and/or by enema. When the radioactive isotope in the ligand decays, it can be measured by PET or SPECT scan imaging. It is often used to quantify the binding of a test molecule to the binding site of radioligand.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

The term "(p,n) reaction" refers to a type of nuclear reaction that occurs when a neutron enters a nucleus and a proton leaves the nucleus simultaneously.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides. In an embodiment, a peptide is 20 amino acids or less in length. In an embodiment, a peptide is 10 amino acids or less in length.

As used herein, a "peptidomimetic" is a compound containing non-peptidic structural elements that is capable of mimicking the biological action of a parent peptide. A peptidomimetic may or may not comprise peptide bonds.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T." "Recombinant polynucleotide" refers to a polynucleotide having sequences that are not naturally joined together. An amplified or assembled recombinant polynucleotide may be included in a suitable vector, and the vector can be used to transform a suitable host cell.

The term "positron emission tomography (PET)" refers to a functional imaging technique that is used to observe metabolic processes in the body. The system detects pairs of gamma rays emitted indirectly by a positron-emitting radioisotope (tracer), which is introduced into the body on a biologically active molecule.

The term "single-photon emission computed tomography (SPECT)" is a nuclear medicine tomographic imaging technique that is used to observe metabolic processes in the body. SPECT is similar to PET in its use of radioactive tracer material and detection of gamma rays. In contrast with PET, however, the tracers used in SPECT emit gamma radiation that is measured directly, whereas PET tracers emit positrons that annihilate with electrons up to a few millimeters away, causing two gamma photons to be emitted in opposite directions.

By the term "specifically binds," as used herein, is meant a molecule, such as a ligand, which recognizes and binds to another molecule or feature, such as a receptor, but does not substantially recognize or bind other molecules or features in a sample.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists. Inhibiting a receptor means reducing a parameter of the receptor's function(s).

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "subject" or "patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

REFERENCES

1. Weiss, $Ca^{2+}$ Permeable AMPA Channels in Diseases of the Nervous System, Frontiers in Molecular Neuroscience 4 (2011): 42, PMC, Web. Aug. 24, 2017.
2. Vandenberghe et al., AMPA Receptor Calcium Permeability, GluR2 Expression, and Selective Motoneuron Vulnerability, The Journal of Neuroscience, Jan. 1, 2000, 20(1):123-132, available at http://www.jneurosci.org/content/jneuro/20/1/123.full.pdf.
3. *PTSD Statistics*, PTSD United, available at http://www.ptsdunited.org/ptsd-statistics-2/.
4. American Psychiatric Association, "Trauma- and Stressor-Related Disorders", *Diagnostic and statistical manual of mental disorders* (5th ed.), Arlington, Va., American Psychiatric Publishing (2013).
5. Majo et al., PET and SPECT tracers for glutamate receptors, Drug Discovery Today, Vol. 18, Issues 3-4, February 2013, pages 173-184, available at http://www.sciencedirect.com/science/article/pii/S1359644612003571.
6. AMPA receptor, Wikipedia, https://en.wikipedia.org/wiki/AMPA_receptor, last accessed Dec. 16, 2016.
7. Park et al., Calcium-Permeable AMPA Receptors Mediate the Induction of the Protein Kinase A-Dependent Component of Long-Term Potentiation in the Hippocampus, Journal of Neuroscience Jan. 13, 2016, 36 (2) 622-631.
8. Perusini, Jennifer Nicole, The Mechanisms of Fear Sensitization Caused by Acute Traumatic Stress: from Induction to Expression to Long-Lasting Reversal, UCLA: Psychology 0780 (2014), retrieved from: http://escholarship.org/uc/item/3578829d.
9. Perusini et al., Induction and Expression of Fear Sensitization Caused by Acute Traumatic Stress, Neuropsychopharmacology, 41: 45-57 (2016).

10. Rau, V., De Cola, J. P., & Fanselow, M. S. (2005). Stress-induced enhancement of fear learning: An animal model of posttraumatic stress disorder. *Neuroscience & Biobehavioral Reviews*, 29, 1207-1223.
11. Rau, V. & Fanselow, M. S. (2009). Exposure to a stressor produces a long lasting enhancement of fear learning in rats. *Stress*, 12, 25-33.
12. Bolshakov et al., Different arrangement of hydrophobic and nucleophilic components of channel binding sites in N-methyl-D-aspartate and AMPA receptors of rat brain is revealed by channel blockade, Neuroscience Letters 291 (2000) 101-104.
13. Morris et al., Diagnostic accuracy of 18F amyloid PET tracers for the diagnosis of Alzheimer's disease: a systematic review and meta-analysis, Eur J Nucl Med Mol Imaging. 2016; 43: 374-385.
14. Olah et al., Ionic Fluorination of Adamantane, Diamantane, and Triphenylmethane with Nitrosyl Tetrafluoroborate/Pyridine Polyhydrogen Fluoride (PPHF), J. Org. Chem., 1983, 48 (19), pp 3356-3358 (September 1983) (DOI: 10.1021/jo00167a050).
15. Rozen and Gal, Direct Synthesis of Fluoro-Bicyclic Compounds with Fluorine, J. Org. Chem., 1988, 53 (12), pp 2803-2807 (June 1988) (DOI: 10.1021/jo00247a026).

What is claimed is:

1. A method of detecting GluA1 levels, or GluA1-containing, GluA2-lacking AMPAR levels, in a region of interest of a subject, comprising:
   a. administering to the subject a first amount of a radiolabeled composition comprising at least one ligand of GluA1 or of a GluA1-containing, GluA2-lacking AMPAR, labeled with a radioactive isotope, wherein the radiolabeled composition comprises any of the following structures:

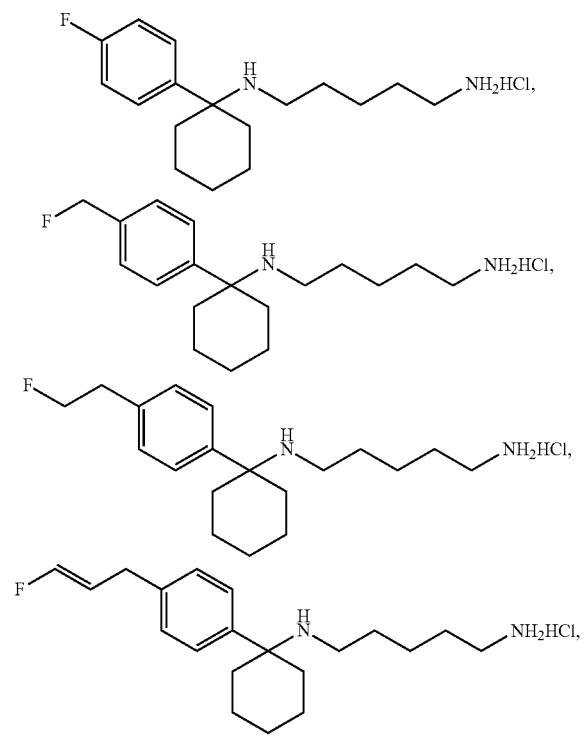

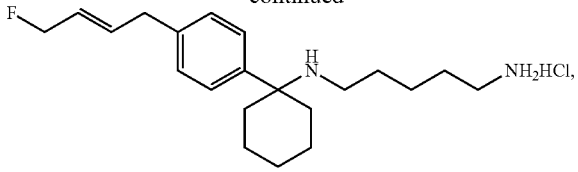

or pharmaceutically acceptable salts thereof, wherein the F is an [$^{18}$F] radioisotope;
   b. subjecting at least the region of interest of the subject to radiological imaging capable of detecting radioactive emissions from an amount of the radiolabeled composition; and
   c. determining or quantifying, based at least in part upon the radiological imaging, an amount of radioactive emissions corresponding to a second amount of the radiolabeled composition that is in the region of interest after administration of the first amount.
2. The method of claim 1, further comprising:
   d. determining or quantifying a GluA1 subunit density or a GluA1-containing, GluA2-lacking AMPAR density in the region of interest of the subject based at least in part upon the amount of radioactive emissions corresponding to the second amount of the radiolabeled composition.
3. The method of claim 2, further comprising:
   e. comparing the density so determined or quantified with a predetermined baseline level, wherein a density different from the predetermined baseline level indicates a GluA1-mediated disorder in the subject.
4. The method of claim 3, wherein the region of interest is an amygdala, and the GluA1-mediated disorder is PTSD.
5. The method of claim 1, wherein the amount of radioactive emissions corresponding to the second amount of the radiolabeled composition corresponds to an amount of binding and localization of the radiolabeled composition in the region of interest, and a difference in binding and localization of the radiolabeled composition in the region of interest compared to a normal subject without a GluA1-mediated disorder is indicative of a GluA1-mediated disorder.
6. The method of claim 1, wherein the subject is a living subject.
7. A compound having the following structure:

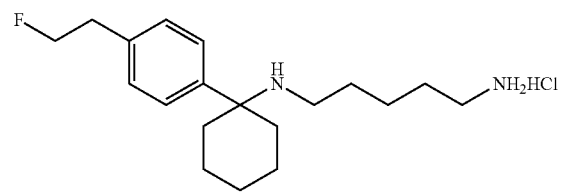

or a pharmaceutically acceptable salt thereof, wherein the F is an [$^{18}$F] radioisotope.
8. The compound of claim 7, wherein the compound is in a pharmaceutically acceptable carrier.
9. The compound of claim 7, wherein the compound is in a solution.
10. The compound of claim 9, wherein the solution is a saline solution.
11. The compound of claim 7, wherein the compound is a ligand of GluA1 or of a GluA1-containing, GluA2-lacking AMPAR.

12. The compound of claim 7, wherein the compound is suitable as a radiolabeled tracer for radiological imaging.

13. The compound of claim 7, wherein the compound serves as an imaging agent suitable for detecting GluA1 levels or GluA1-containing, GluA2-lacking AMPAR levels in a region of interest of a subject.

14. A compound having the following structure:

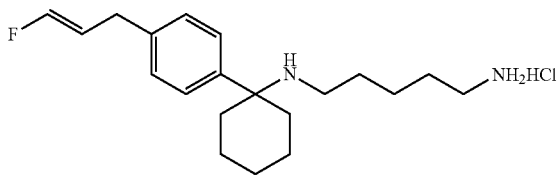

or a pharmaceutically acceptable salt thereof, wherein the F is an [$^{18}$F] radioisotope.

15. The compound of claim 14, wherein the compound is in a pharmaceutically acceptable carrier.

16. The compound of claim 14, wherein the compound is in a solution.

17. The compound of claim 16, wherein the solution is a saline solution.

18. The compound of claim 14, wherein the compound is a ligand of GluA1 or of a GluA1-containing, GluA2-lacking AMPAR.

19. The compound of claim 14, wherein the compound is suitable as a radiolabeled tracer for radiological imaging.

20. The compound of claim 14, wherein the compound serves as an imaging agent suitable for detecting GluA1 levels or GluA1-containing, GluA2-lacking AMPAR levels in a region of interest of a subject.

* * * * *